(12) United States Patent
Berlin et al.

(10) Patent No.: US 12,583,892 B2
(45) Date of Patent: Mar. 24, 2026

(54) CONUS-BASED TOXIN PEPTIDES, NUCLEIC ACIDS ENCODING SAME AND USES THEREOF IN MODULATING NMDA RECEPTORS

(71) Applicant: TECHNION RESEARCH AND DEVELOPMENT FOUNDATION LIMITED, Haifa (IL)

(72) Inventors: Shai Berlin, Haifa (IL); Ido Carmi, Haifa (IL); Shaden Zoabi, Haifa (IL)

(73) Assignee: TECHNION RESEARCH AND DEVELOPMENT FOUNDATION LIMITED, Haifa (IL)

( * ) Notice: Subject to any disclaimer, the term of this patent is extended or adjusted under 35 U.S.C. 154(b) by 940 days.

(21) Appl. No.: 17/851,430

(22) Filed: Jun. 28, 2022

(65) Prior Publication Data

US 2022/0324922 A1 Oct. 13, 2022

Related U.S. Application Data

(63) Continuation of application No. PCT/IL2021/050013, filed on Jan. 5, 2021.

(60) Provisional application No. 62/957,240, filed on Jan. 5, 2020.

(51) Int. Cl.
*C07K 14/435* (2006.01)
*A61K 48/00* (2006.01)
*A61P 25/28* (2006.01)

(52) U.S. Cl.
CPC ...... *C07K 14/43504* (2013.01); *A61K 48/005* (2013.01); *A61P 25/28* (2018.01); *C07K 2319/03* (2013.01)

(58) Field of Classification Search
CPC ............ C07K 14/435; C07K 14/43504; C07K 2319/03
See application file for complete search history.

(56) References Cited

U.S. PATENT DOCUMENTS

| | | |
|---|---|---|
| 5,844,077 A | 12/1998 | Saydoff |
| 9,163,094 B2 | 10/2015 | Schmidt et al. |
| 10,689,418 B2 | 6/2020 | Reyes Montaño et al. |
| 2003/0065138 A1* | 4/2003 | Olivera et al. ........... C07K 7/08 530/324 |
| 2006/0057614 A1* | 3/2006 | Heintz ..................... G01N 1/28 435/6 |
| 2019/0085028 A1* | 3/2019 | Reyes Montaño et al. ................. C07K 7/08 |

FOREIGN PATENT DOCUMENTS

| | | |
|---|---|---|
| WO | 1996/11698 | 4/1996 |
| WO | 02072005 A2 | 9/2002 |
| WO | 2018136614 A1 | 7/2018 |

OTHER PUBLICATIONS

Gowd et al. (2008) "Conantokin-P, an unusual conantokin with a long disulfide loop" Toxicon, 52(2), 203-213. (Year: 2008).*
Hardingham et al (2010) Synaptic versus extrasynaptic NMDA receptor signalling: implications for neurodegenerative disorders, Nature Reviews Neuroscience, 11(10):682.
Lewis et al (2012) Conus venom peptide pharmacology, Pharmacological reviews, 64(2):259-29.
Parsons et al (2014) Extrasynaptic NMDA receptor involvement in central nervous system disorders, Neuron, 82(2):279-293.
Sun et al (2018) The Differences between GluN2A and GluN2B signaling in the brain, Journal of neuroscience research, 96(8):1430-1443.
Sambrook et al (2001) Molecular Cloning: a Laboratory Manual, Cold Springs Harbor Laboratory Press, New York.
International Search Report and Written Opinion of PCT/IL2021/050013 Completed Mar. 17, 2021; Mailed Mar. 17, 2021 13 Pages.
Gowd et al (2008) Conantokin-P, an unusual conantokin with a long disulfide loop, Toxicon 52(2):203-213.
Lebbe et al (2016) In the picture: disulfide-poor conopeptides, a class of pharmacologically interesting compounds, Journal of Venomous Animals and Toxins including Tropical Diseases, 22(1).

* cited by examiner

*Primary Examiner* — James Joseph Graber
(74) *Attorney, Agent, or Firm* — The Roy Gross Law Firm, LLC; Roy D. Gross

(57) ABSTRACT

Provided herein are modified forms of Conantokin peptides, including, modified Con-P peptides, nucleic acids encoding the same and compositions thereof. Further provided are nucleic acid molecules encoding for chimeric modified conantokin polypeptides to be expressed in or on a membrane of a target cells, compositions comprising the same and uses thereof for treating various neurodegenerative conditions.

16 Claims, 13 Drawing Sheets
(13 of 13 Drawing Sheet(s) Filed in Color)
Specification includes a Sequence Listing.

Fig. 1A
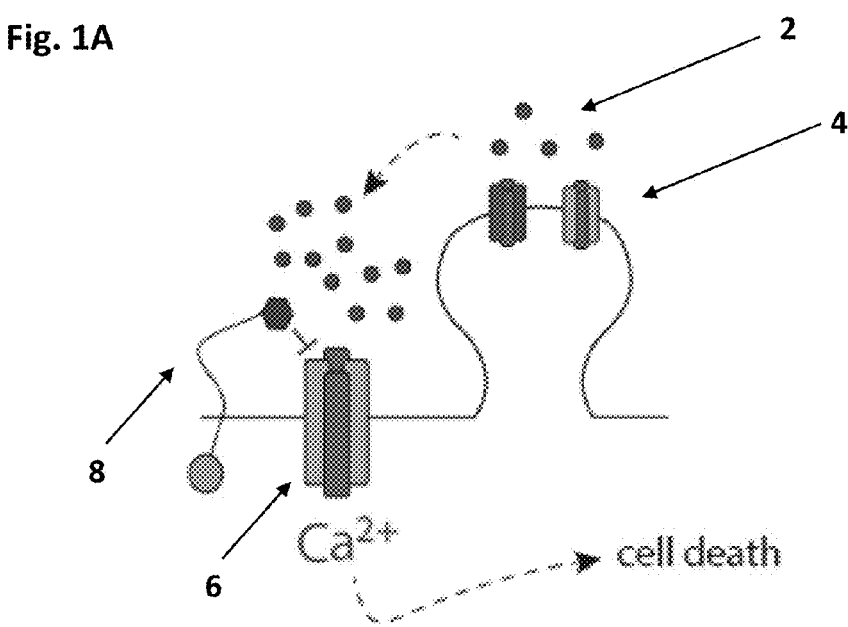
Fig. 1B
Fig. 2
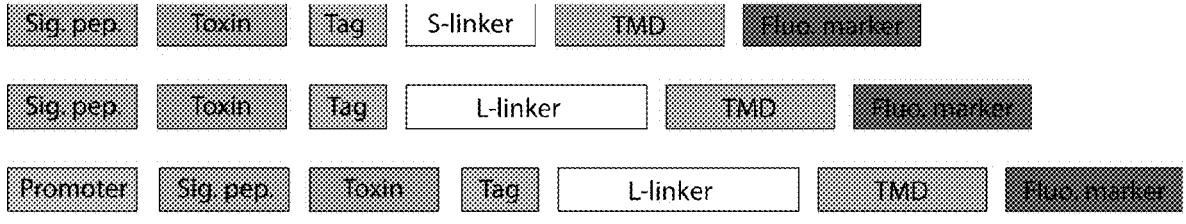

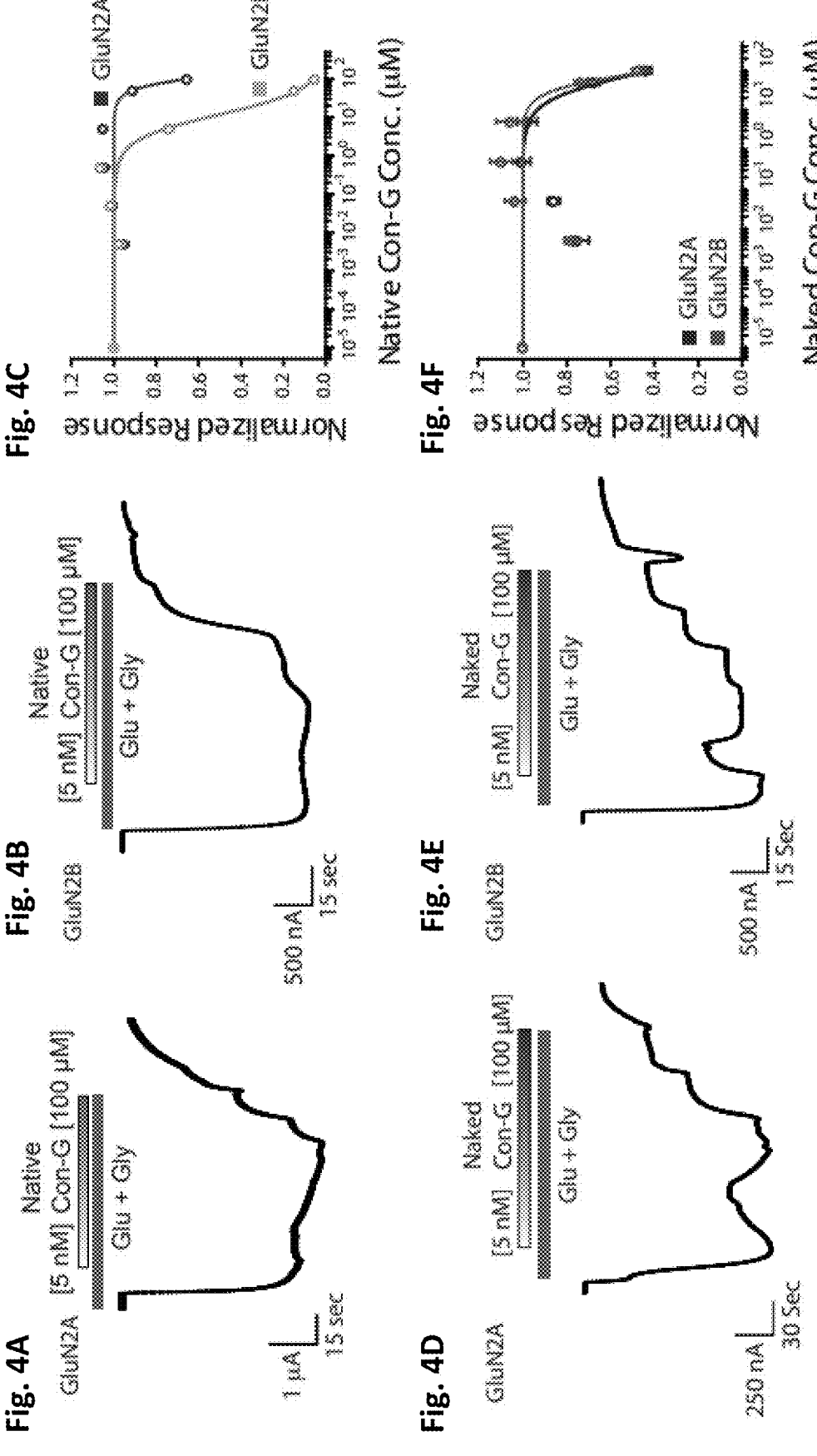

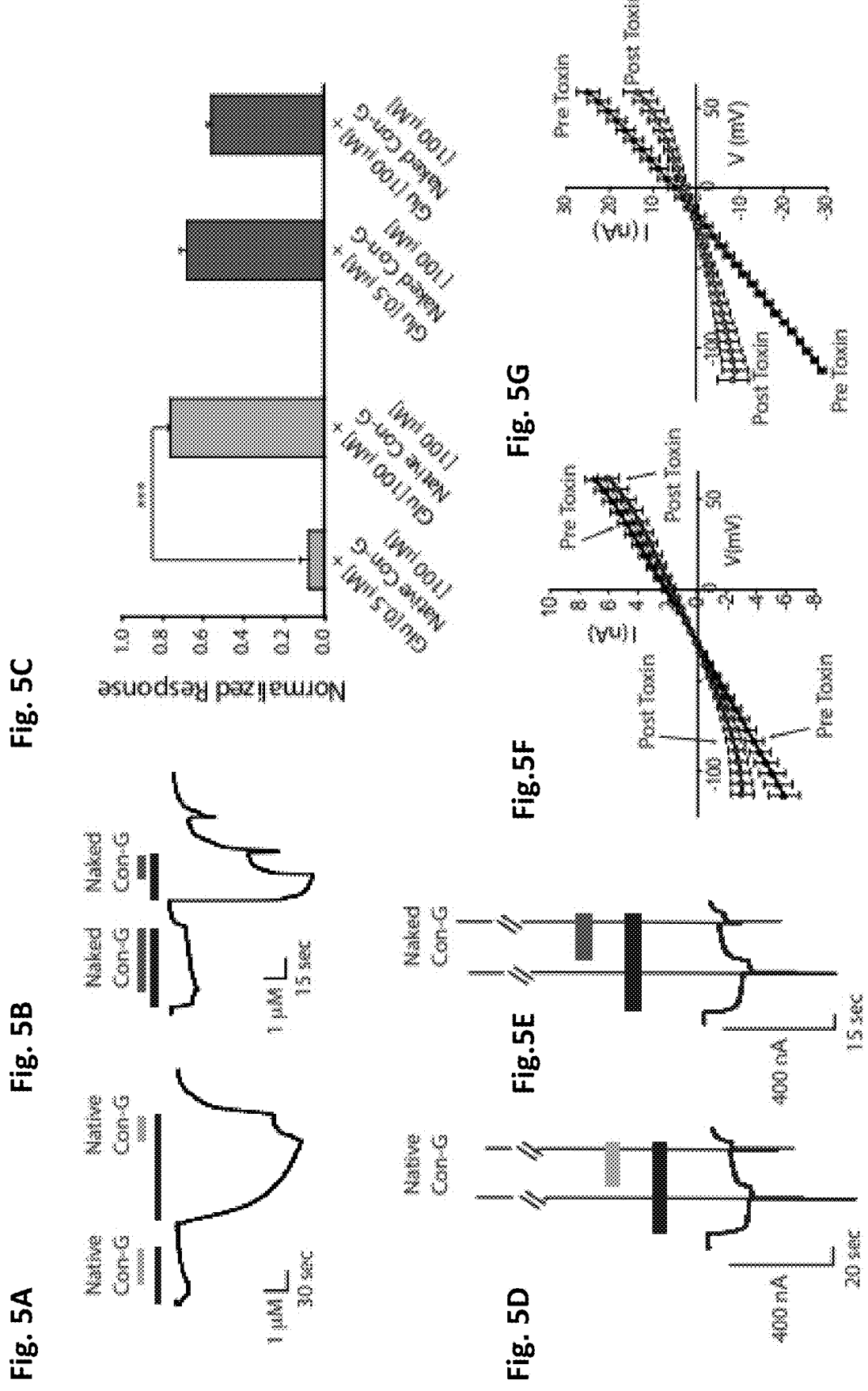

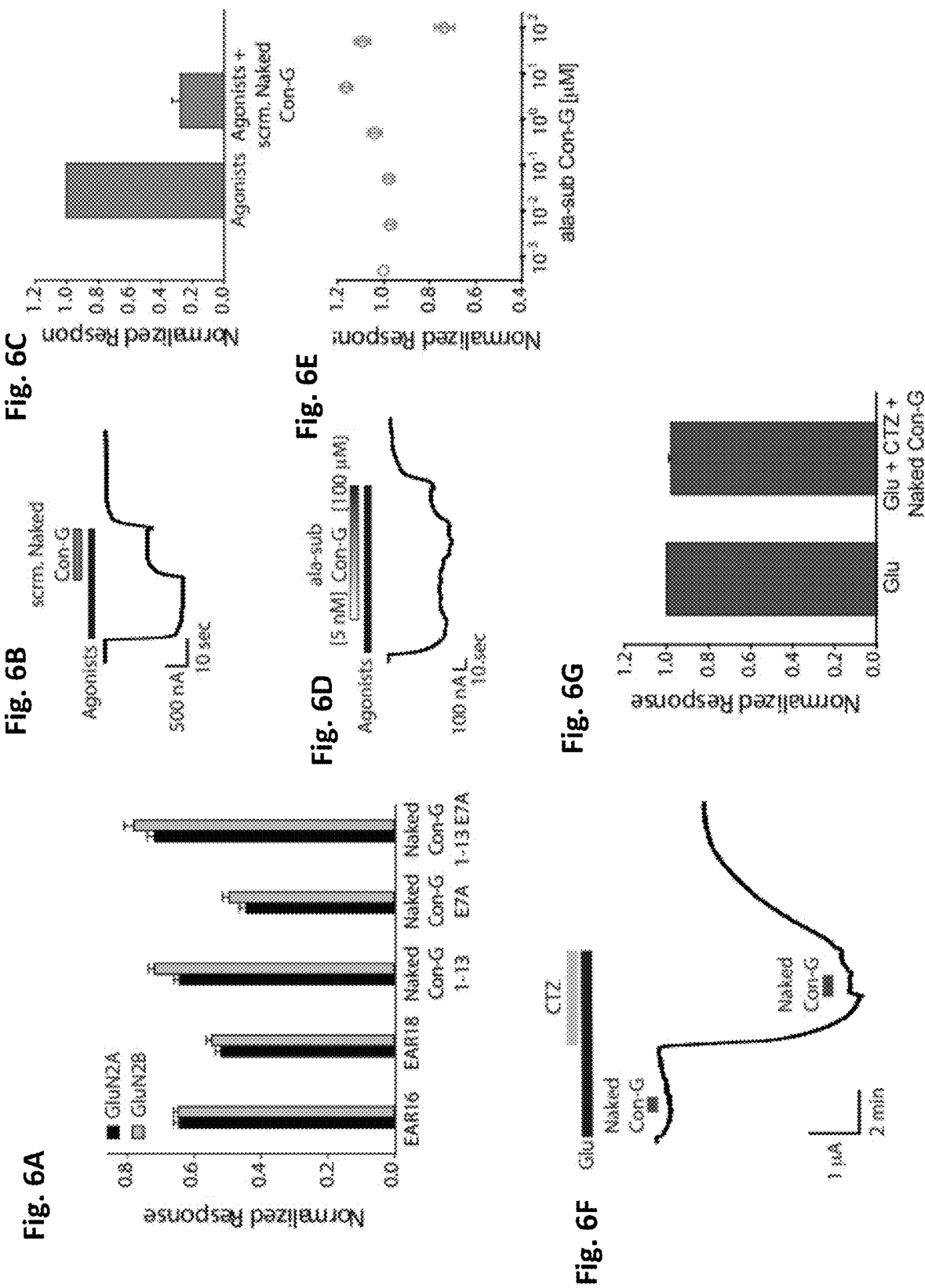

Fig. 7B                    Fig. 7C

Fig. 10A
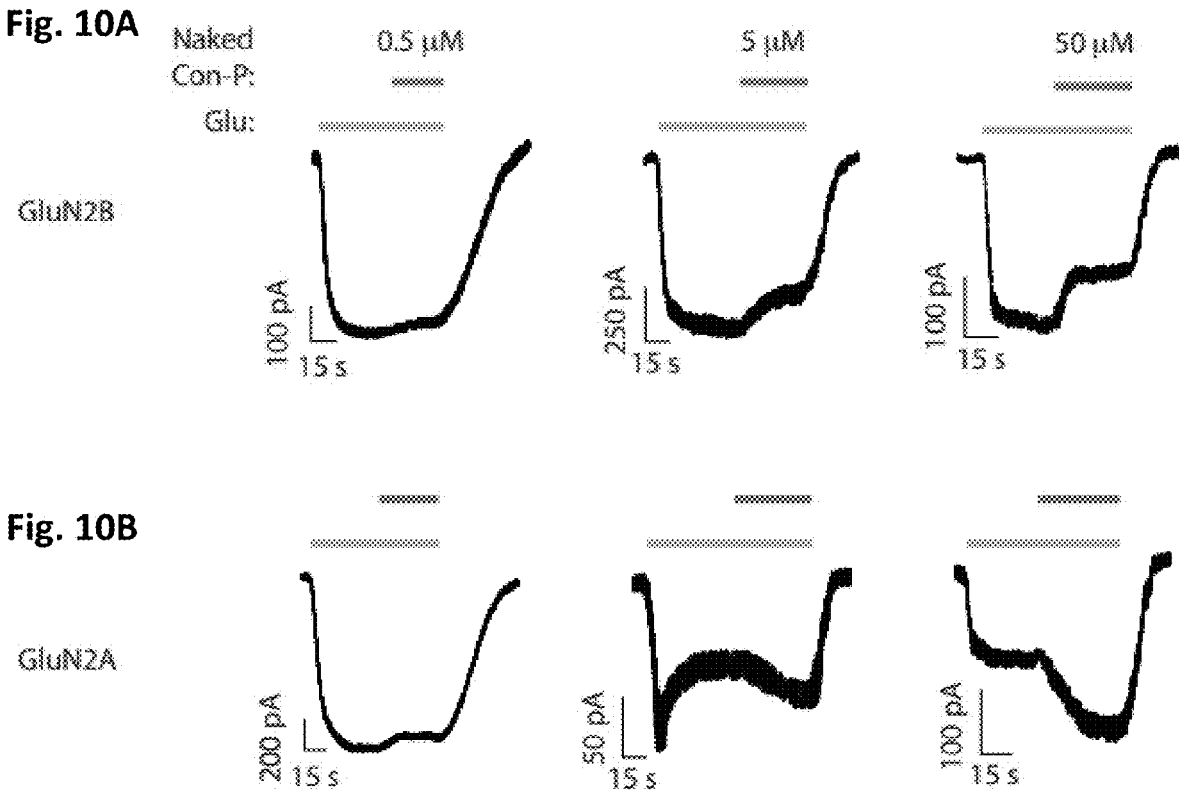
Fig. 10B
Fig. 10C
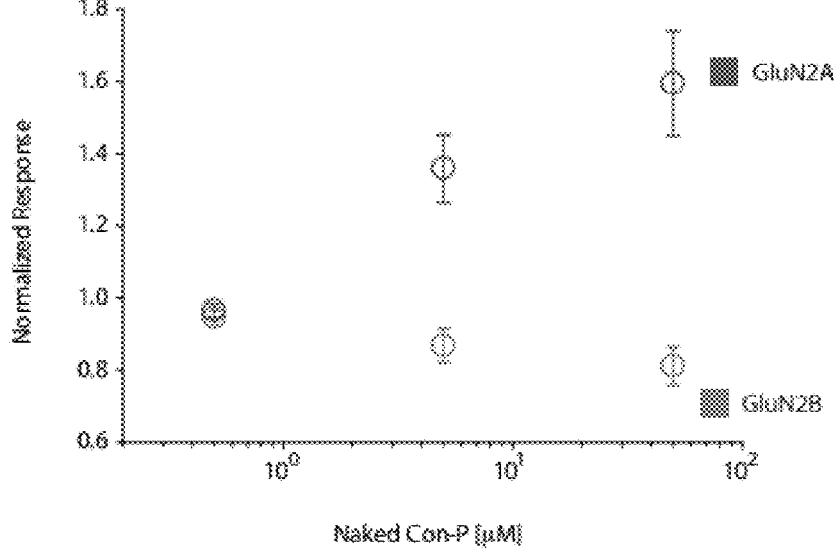

Fig. 14A
GluN1a/2B
con-G$_{mem}$
membrane
RFP
glutamate
Fig. 14B
5 µm
Fig. 14C
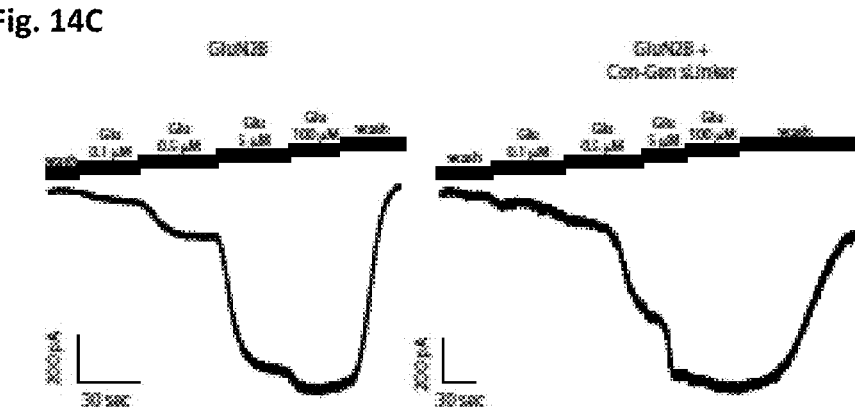
Fig. 14D
Fig. 14E
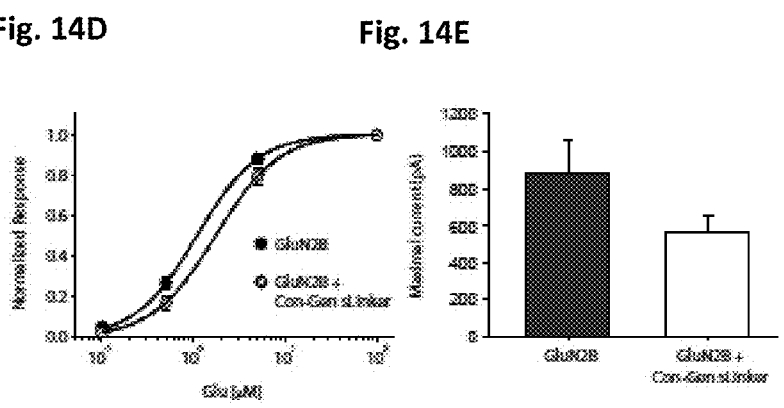

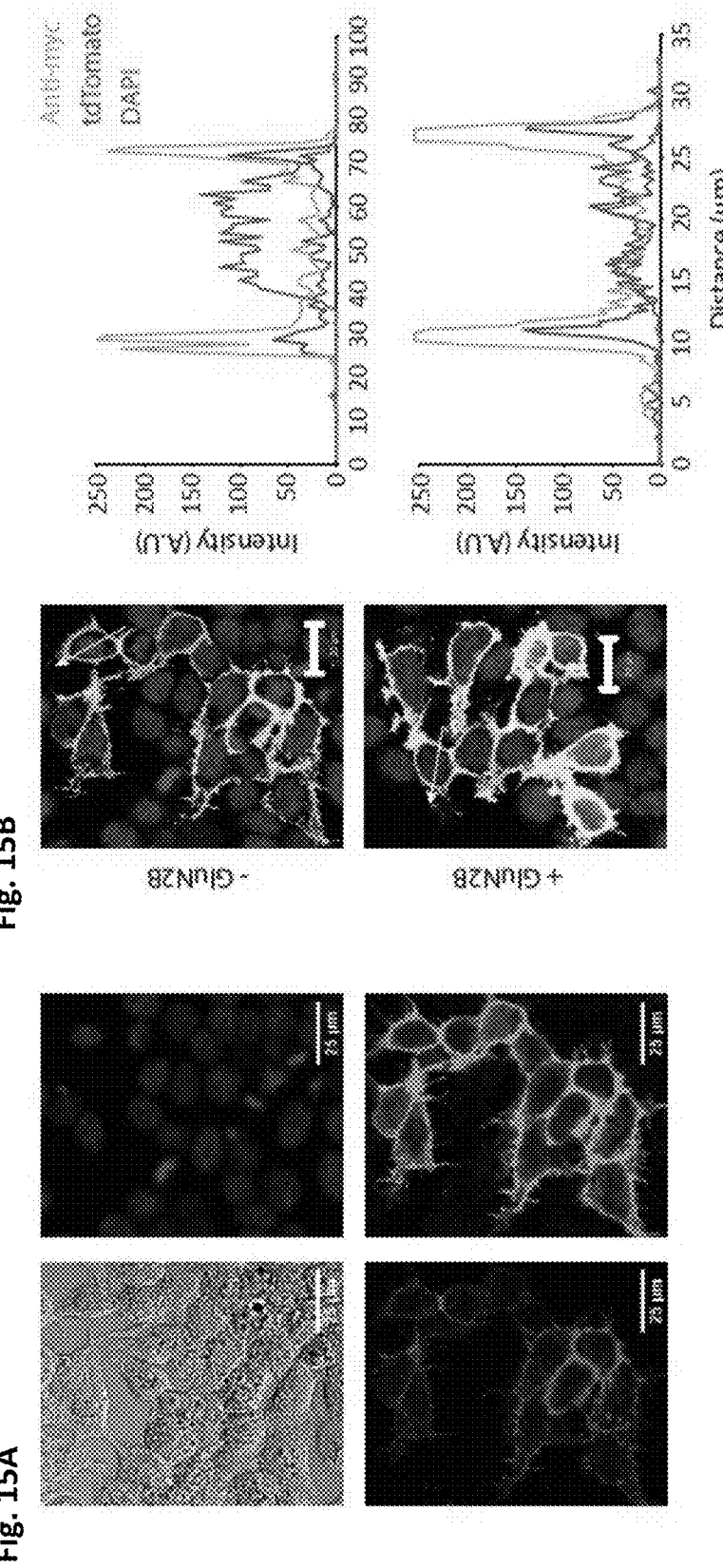

CONUS-BASED TOXIN PEPTIDES, NUCLEIC ACIDS ENCODING SAME AND USES THEREOF IN MODULATING NMDA RECEPTORS

CROSS REFERENCE TO RELATED APPLICATIONS

This application is a Bypass Continuation of PCT Patent Application No. PCT/IL2021/050013, having International filing date of Jan. 5, 2021, which claims the benefit of priority of U.S. Provisional Patent Application No. 62/957, 240, filed Jan. 5, 2020, the contents of which are all incorporated herein by reference in their entirety.

FIELD OF THE INVENTION

The present invention relates to non-naturally occurring *Conus*-based toxin peptides and chimeric polypeptides and nucleic acid molecules encoding the same. The invention further relates to compositions for expressing the Conus-based toxin peptides and uses thereof in modulating N-methyl-D-aspartate receptor (NMDA) receptors, for treating neurodegenerative conditions.

BACKGROUND OF THE INVENTION

Pharmacological treatment for Alzheimer's Disease (AD) and other neurodegenerative conditions is currently insufficient due to lack of specificity of targeted afflicted cells and brain regions, which result in severe side effects. There are, in fact, no current available treatments capable of preventing degeneration of neurons.

Current drugs focus on inhibition of two main neurotransmitter systems; Acetylcholine and glutamate, via inhibition of the acetylcholine esterase (Donepezil, Galantamine, Rivastigmine which are FDA approved compounds) or direct inhibition of all types of the N-methyl-D-aspartate receptor (NMDAR) by Memantine (FDA approved), respectively. These drugs have several shortcomings, first, they must cross the blood brain barrier thus making it hard to determine brain levels of the drug at the site of interest, namely the synapse and extrasynaptic regions. Second, they lack cellular and subunit specificity (in the case of NMDARs), explicitly inflicting both diseased and healthy cells and cannot target specific receptor subtypes. Together, they disrupt the normal homeostasis of all cells. In addition, none of the treatments stop the inevitable deterioration and death of neurons. Consequently, patients may suffer from various and severe side effects.

Excitotoxicity is a collection of cellular processes leading, inter alia, to aberrant calcium homeostasis and initiation of downstream pathways, resulting in cell death. In the brain, excitotoxicity is common to many pathologies, such as ischemic stroke, traumatic brain injury and, particularly, neurodegenerative diseases (NDs) such as Alzheimer's Disease (AD), Parkinson's Disease (PD) and Amyotrophic Lateral Sclerosis (ALS). It is emerging that, despite major etiological differences between neurodegenerative diseases, many of these diseases converge onto a common mechanism involving excessive opening of the N-Methyl-D-Aspartate Receptors (NMDARs).

The NMDAR (also referred to as GluNR) is an ionotropic glutamate receptor, mostly found in excitatory synapses along neuronal dendritic arbors. It is a non-selective, heterotetrameric cation-channel (importantly, conducts Ca2+) that is formed by different combinations of subunits (GluN1, GluN2A-D and GluN3A-B). Notably, each receptor subtype exhibits unique biophysical and pharmacological properties and differential distribution patterns (for example, across the brain, during development and as a result of synaptic plasticity), allowing them to play different roles at the synapse. Aside their prototypical roles in mediating different forms of synaptic plasticity, NMDARs are also involved in cell protection and survival pathways, and, paradoxically, in neuronal excitotoxicity and cell death. The different outcomes are thought to be determined by two main factors: subcellular location of the receptors and receptor subtype. More specifically, in terms of location, synaptic NMDARs (sy-NMDARs) are linked to survival pathways (e.g., induction CREB-activity, upregulation of brain-derived-neurotrophic-factor and inhibition of apoptotic pathways, whereas extrasynaptic NMDARs (ex-NMDARs) facilitate neuronal death by downregulating CREB, inducing mitochondrial dysfunction and promote pro-apoptotic pathways. In terms of subtype, in the adult brain, GluN2B-receptors dominate extrasynaptic regions, whereas sy-NMDARs mostly include GluN2A-containing receptors (GluN2A-receptors). Thus, GluN2B is implicated as driving excitotoxicity. The intracellular tail of GluN2B-subunits enhances NMDAR-mediated excitotoxicity and GluN2B subtype-selective antagonists show protective features against apoptosis and degeneration. Models of AD also describe a strong link between Amyloid-beta (Aβ, which is a hallmark of AD) and excessive activation of ex-GluN2B-containing receptors. Together, it is suggested that excessive glutamate at the synaptic cleft (due to inhibition of glutamate reuptake, clearance or neuronal hyperexcitability, and the lie) results in unwarranted glutamate spillover to extrasynaptic regions, leading to excessive activation of ex-GluN2B-containing receptors and cell death.

The involvement of ex-GluN2B-receptors in excitotoxicity has prompted clinical studies using diffusible inhibitors of GluN2B-receptors, however all of the first-generation trials failed due to narrow therapeutic windows and intolerable side-effects. The main cause for failure was attributed to poor subunit-selectivity of the drugs and the non-restricted inhibition of NMDARs across the entire brain, leading to disruption of vital synaptic activity of NMDARs. The use of more potent and selective GluN2B-antagonists (such as ifenprodil) was also unsuccessful, for similar reasons: the drug diffused and affected all receptors across the brain, instead of solely targeting ex-GluN2B receptors located on afflicted cells, in select brain regions. In the case of AD, memantine is the only FDA-approved NMDAR-targeting compound. One of the reasons is that memantine exhibit mild selectivity towards ex-NMDARs, over sy-NMDARs. It should be noted, however, that despite the advantages and clinical tolerance of memantine over other drugs, its efficiency remains disputed, and cannot be restricted to target ex-NMDARs of the GluN2B-type in neurons, affected by the disease. Similar failures are seen with other non-competitive, low affinity NMDAR inhibitors in Parkinson's' disease (PD) research.

Conantokins are a family of small (helical) peptides, derived from the venom of predatory marine snails of the genus Conus. Conantokins are the only naturally-derived peptides known to act as potent and specific antagonists of the N-methyl-D-aspartate receptor (NMDAR), as they exhibit both receptor- and subunit-selectivity. Conantokins are small helical peptides of low potency inhibition (IC50~μM) of various NMDAR-subunits. Several subtypes of conantokins have been identified, based on the species from which they are derived. The conantokins are unique in that they possess several gamma-carboxyglutamyl (Gla) residues, generated by the post-translational modification of glutamyl (Glu) residues. These Gla residues are thought to be important for the structure and function of the peptide and conformational changes thereof. Subtypes of conantokin include: Conantokin-G (Con-G), which is a small peptide isolated from the fish-hunting snail, Conus geographus. This peptide has 5 Gla residues. For example, Con-G may act as a neuroprotective agent in ischemic and excitotoxic brain injury, neuronal apoptosis, pain, epilepsy, and as a research tool in drug addiction and Alzheimer's disease. Con-G blocks NMDAR-mediated excitatory postsynaptic currents (EPSCs), can reduce the strength of excitotoxic intracellular $Ca^{2+}$ actions; Conantokin-T Con-T, which is purified from the venom of the fish-hunting cone-snail, Conus tulipa. This peptide has 4 residues of Gla. Con-T acts by inhibiting NMDAR-mediated Ca2+ influx in neurons in the central nervous system; Conantokin-R (Con-R) is derived from Conus radiatus; and Conantokin-L (Con-L) is derived from Conus lynceus. Con-L differs from Con-R in the C-terminal amino acids; Conantokin-Pr1, -Pr2 and -Pr3 are derived from the species Conus parius; Conantokin-P (Con-P) is found in fish-hunting cone snails, Conus purpurascens; and Conantokin-E (Con-E) is found in fish-hunting cone snails Conus ermineus; Conantokin-R1-A (Con-R1A) Is derived from the venom of Conus rolani; Conantokin-Br (or conantokin-S1) is derived from the Conus brettinghami (Conus sulcatus).

The conantokins exhibit a variability of selectivity across the NMDAR subunits, suggesting their development as subunit-specific pharmacological agents. For example, U.S. Pat. No. 10,689,418 is directed to synthetic peptides that modulate the NMDA receptor. For example, US Patent Application publication No. US 20060057614 is directed to tethering neuropeptides and toxins for modulation of ion channels and receptors.

Nevertheless, there is a need in the art for modified conantokin peptides which can act as selective modulators of NMDA receptors, in particular, of GluN2B, in a desired spatial and/or temporal mode, in in-vivo context, that can be used for a for safe, efficient and cost-effective treatment of various neurodegenerative conditions.

SUMMARY OF THE INVENTION

According to some embodiments, there are provided advantageous, selective modulators of NMDA receptor, and in particular, GluN2 subunits, which can act in a spatial and/or temporal fashion in neuronal tissues, such as, synapse regions, to exert a beneficial effect on the activity of the synapses, for treating various neurodegenerative conditions. According to some embodiments, the selective modulators disclosed herein are at least partially based on conantokin derived peptides, while including one or amino acid substitutions as compared to naturally occurring conantokin peptides. Further provided herein are composition comprising chimeric conantokin-modified polypeptides, nucleic acids encoding the same and expression vectors capable of inducing expression of the conantokin-modified peptides at a desired spatial and/or temporal pattern in target cells. According to some embodiments, further provided herein are methods of treating various neurodegenerative conditions utilizing the advantageous modulators of the present disclosure.

According to some embodiments, the modified peptides disclosed herein are advantageous as they unexpectedly exhibit a combination of beneficial traits, including: selectivity of inhibition (for example, only of GluN2B-receptors); spatially-limited activity (for example, action at a desired location (tissue/cell/cellular compartment), such as, at the extra synapse region of neurons)); temporally-limited (expression or activity only at times of excessive spillover or when neuronal degeneration has been initiated); and/or exhibit additional beneficial activity (for example, inducing activity of GluN2A-receptors). Such advantageous agents are highly beneficial, since not only can they specifically inhibit undesired activity of receptor subtypes and in spatial and/or temporal pattern, they can also preserve or even potentiate (increase) the activity of other beneficial subunits in the same spatial-temporal milieu (for example, synaptic or extrasynaptic) in healthy brain regions and cells. Thus, the advantageous agents disclosed herein (modified peptides, chimeric polypeptides, compositions including the same and/or nucleic acid molecules encoding the same) can be used in providing enhanced beneficial effect, with reduced side effects, which is cost effective.

According to some embodiments, provided herein are modified short peptide toxins from the Conus snail family (Conantokins) as specific blockers of different subunits of the NMDAR receptor. In some embodiments, the modified peptides disclosed herein are genetically-encoded utilizing nucleic acid molecules encoding the same, to facilitate/promote their membrane expression in a spatial and/or temporal manner in target cell (for example, exclusively/only in diseased neurons (for example, neurons in which apoptosis has been initiated)). Thus, in some embodiments, the expression of the advantageous chimeric modified peptides, which exhibit specificity towards the NR2B (GluN2B) subunits of the NMDA receptor, may be exclusively (solely) to the extrasynapse, thus sparing all other subunits and normal synaptic activity. Moreover, imparting expression of the peptides under the control of specific promoters (such as, for example, apoptotic promoters), can further enable the expression of the modified peptides exclusively in neurons in which the apoptotic process has already been initiated, while sparing, or not affecting healthy neurons (since the modified peptides will not be expressed therein). Thus, the advantageous compositions and method disclosed herein can reduce excessive NMDAR-activation and reduce excessive Ca2+-entry into neurons, which are the main drivers for apoptosis. These would ultimately ameliorate cognitive deficits and further decline related to neurodegenerative conditions, such as, AD, PD, HD, and ALS.

According to some embodiments, the currently disclosed advantageous modified peptides can overcome current shortcomings of neurodegenerative diseases' treatment by targeting specific afflicted cell populations in the brain, halting apoptosis, while maintaining normal neuronal function. In some embodiments, without wishing to be bound by any theory or mechanism, this is facilitated by the traits of the soluble modified peptides, and/or by utilizing the genetically engineered highly selective membrane-associated chimeric modified Con-peptides for inhibition of a central hub of excitotoxicity, in particular, extrasynaptic GluN2B (NR2B)-containing NMDARs.

According to some embodiments, the modified peptides disclosed herein and the nucleic acids encoding the same can further enable to study the involvement of synaptic vs. extrasynaptic subunits in neurodegeneration, as well as being a novel therapeutic approach for treating neurodegenerative conditions, such as, AD.

Thus, according to some embodiments, the advantageous modified Con-peptides disclosed herein each have a set of unique features (inhibition, potentiation, full agonism), rendering them useful (individually or in combination) in reducing neuronal excitation by inhibiting ex-GluN2B-receptors, enhance synaptic 2A receptors and/or activate presynaptic GABAbRs.

According to some embodiments, the advantageous modified/non-naturally occurring conantokin peptides include at least one amino acid modification/replacement/substitution and/or deletion (truncation) of a stretch of amino acids, compared to a WT, unmodified, naturally occurring corresponding conantokin peptide.

According to some exemplary embodiments, the modified conantokin is conantokin G (Con-G). In some embodiments, the modified conantokin is conantokin-P (Con-P). In some embodiments, the modified conantokin is conantokin-Pr3. In some embodiments, the modified conantokin peptide is a peptide having at least some sequence similarity to Con peptide. In some embodiments, such related Con peptide is a peptide derived from mammalian Amyloid-Precursor-Protein (APP) and which can act as an NMDA modulator, as exemplified herein.

According to some embodiments, provided herein are methods and compositions for treatment of neurodegenerative condition, the methods include administration of a pharmaceutical composition including the modified peptides of the present disclosure, or constructs expressing the same, to a subject in need thereof. In some embodiments, the neurodegenerative condition is selected from Alzheimer's Disease (AD), Parkinson's Disease (PD), Amyotrophic Lateral Sclerosis (ALS), and Huntington's disease (HD).

According to some embodiments, there is provided a modified conantokin-P (con-P) peptide having at least one amino acid residue substitution as compared to the naturally occurring native conantokin-P peptide (represented by SEQ ID NO:1).

According to some embodiments, the amino acid substitution includes substitution of at least one gamma carboxyglutamate acid (Gla) residue of the naturally occurring conantokin-P.

According to some embodiments, the amino acid substitution may include substitution of five gamma carboxyglutamate acid residues of the naturally occurring conantokin-P.

According to some embodiments, the amino acid substitution may include substitution of a gamma carboxyglutamate acid residue of the naturally occurring conantokin-P with an amino acid selected from the group consisting of: Aspartate, Alanine, Glycine and Glutamate. Each possibility is a separate embodiment.

According to some embodiments, the amino acid substitution may include substitution of a gamma carboxyglutamate acid residue of the naturally occurring conantokin-P with Glutamate or Aspartate.

According to some embodiments, the modified con-P peptide has an amino acid sequence as denoted by any of SEQ ID NOs: 4-7. Each possibility is a separate embodiment.

According to some embodiments, the modified con-P peptide is capable of modulating activity of GluN2B NMDA receptor subunit and/or GluN2A NMDA receptor subunit in cells.

According to some embodiments, the modulation is spatial and/or temporal.

According to some embodiments, the modulation includes reducing activity of GluN2B receptor subunit and/or increasing activity of GluN2A receptor subunit.

According to some embodiments, the modified con-P peptide is capable of inhibiting activity of GluN2B receptor subunit when expressed in extrasynaptic region of neuronal cells and/or wherein the modified con-P peptide is capable of enhancing activity of GluN2A receptor subunit in the synaptic region of neuronal cells.

According to some embodiments, there is provided a composition including the isolated modified con-P peptide as disclosed herein.

According to some embodiments, the modified polypeptide as disclosed herein, or the composition comprising the same may be used in treating a neurodegenerative condition in a subject in need thereof.

According to some embodiments, there is provided a nucleic acid molecule encoding the modified con-P peptide as disclosed herein. In some embodiments, the nucleic acid molecule may have a nucleotide sequence as denoted by SEQ ID NOs: 17-20.

According to some embodiments, there is provided a vector including the nucleic acid molecule encoding the modified con-P peptide.

According to some embodiments, the vector is an expression vector, further including one or more additional nucleic acid sequences selected from: regulatory sequences, localization sequence, a tag sequence, a marker sequence, or combinations thereof.

According to some embodiments, at least one of the additional nucleotide sequences is in-frame with the nucleotide sequence encoding the modified con-P peptide.

According to some embodiments, the regulatory sequence comprises a promoter, selected from a tissue specific promoter, inducible promoter or a constitutive promoter.

According to some embodiments, the localization sequence may include a transmembrane domain.

According to some embodiments, the tag sequence encodes for a tag selected from: His-tag, Myc-tag, HA-tag and FLAG-tag.

According to some embodiments, the marker sequence encodes for a fluorescent marker protein, such as, GFP, BFP, Cherry Red, dsREd, and the like.

According to some embodiments, nucleic acid molecule encoding for the modified Con-P peptide, or the vector including the same may be used in treating a neurodegenerative condition in a subject in need thereof.

According to some embodiments, there is provided a method of treating neurodegenerative condition in a subject in need thereof, the method includes administering to the subject in need there of a therapeutically effective amount of the modified Con-P peptide, or the composition comprising the same.

According to some embodiments, there is provided a method of treating neurodegenerative disorder in a subject in need thereof, the method includes administering to the subject in need thereof a therapeutically amount of the nucleic acid molecule encoding for the modified Con-P peptide, or the vector including the same.

According to some embodiments, there is provided a vertebrate host cell harboring or expressing the nucleic acid molecule encoding for the modified Con-P peptide.

According to some embodiments, there is provided a host cell transformed or transfected with the vector.

According to some embodiments, there is provided a vertebrate host cell harboring the modified Con-P peptide as disclosed herein. In some embodiments, the host cell is a neuronal cell. In some embodiments, the host cell is an in-vitro cell, or an in-vivo cell.

According to some embodiments, there is provided a nucleic acid molecule for expressing a chimeric modified conantokin polypeptide in or on a membrane of a target cell, the nucleic acid molecule includes:

a first nucleotide sequence encoding for a modified conantokin peptide;

a second nucleotide sequence encoding for a transmembrane domain, capable of directing the expressed modified peptide to the membrane; and a third nucleotide sequence, being a regulatory sequence capable of affecting expression of the modified conantokin peptide within the target cell.

According to some embodiments, the nucleic acid molecule for expressing a chimeric modified conantokin polypeptide may further include one or more nucleic acid sequences encoding for: a signal peptide, a marker sequence, and/or a tag sequence.

According to some embodiments, the nucleic acid molecule for expressing a chimeric modified conantokin polypeptide may further include a linker sequence.

According to some embodiments, the modified conantokin peptide moiety of the chimeric modified conantokin polypeptide is selected from: a modified con-G-peptide, a modified con-P peptide, a modified Con-Pr3 peptide and/or cAPP. Each possibility is a separate embodiment.

According to some embodiments, the modified conantokin peptide include one or more amino acid modifications compared to a corresponding naturally occurring conantokin peptide.

According to some embodiments, the modified conantokin peptide encoded by the first nucleotide sequence has an amino acid sequences as denoted by one or more of: SEQ ID NOs: 4-13 or 14.

According to some embodiments, the first nucleotide sequence encoding for the modified conantokin peptide has a nucleotide sequence as denoted by any one of SEQ ID NOs. 17-26 or 27.

According to some embodiments, the transmembrane domain (TMD) encoded by the second nucleotide sequence is a TMD derived from the PDGF receptor and comprises an amino acid sequence as denoted by SEQ ID NO:37.

According to some embodiments, the second nucleotide sequence may be located downstream of the first nucleotide sequence.

According to some embodiments, the third nucleotide sequence may be a promoter sequence derived from a promoter of an apoptotic gene or a gene related to neurodegeneration. In some embodiments, the third nucleotide sequence may be a promoter sequence derived from a promoter sequence of one or more of: RASGEF1B, SLC26A3, LINGO, GNAI2, NEK6, UBE2D3, CDC42EP4, ERCC3, BBC3, FOXO1, CASP3, CLCA1, CMV, CAG, hSyn, GFAP, and the like. Each possibility is a separate embodiment. According to some embodiments, the third nucleotide sequence may affect the temporal and/or spatial expression of the chimeric polypeptide in target cells or target tissue.

According to some embodiments, the tag sequence may encode for a tag selected from: His-tag, Myc-tag, HA-T-tag and FLAG-tag, and the like.

According to some embodiments, the marker sequence may encode for a fluorescent marker protein, such as, but not limited to: GFP, BFP, dsRed, Cherry red, and the like.

According to some embodiments, the nucleic acid molecule for expressing a chimeric modified conantokin polypeptide is an expression cassette of a viral expression vector.

According to some embodiments, the target cell is a neuronal cell.

According to some embodiments, the membrane is a cellular membrane or an intracellular membrane.

According to some embodiments, the chimeric polypeptide encoded by the nucleic acid is capable of modulating activity of one or more subunits of NMDA receptor. In some embodiments, modulation includes reducing activity of GluN2B receptor subunit and/or increasing activity of GluN2A receptor subunit.

According to some embodiments, the nucleic acid molecule for expressing a chimeric modified conantokin polypeptide may be for use in treating a neurodegenerative condition in a subject in need thereof.

According to some embodiments, there is provided a method of treating neurodegenerative condition in a subject in need thereof, the method includes administering to the subject a therapeutically effective amount of the nucleic acid molecule for expressing a chimeric modified conantokin polypeptide.

According to some embodiments, there is provided a host cell including the nucleic acid molecule for expressing a chimeric modified conantokin polypeptide.

According to some embodiments, there is provided a chimeric polypeptide encoded by the nucleic acid for expressing a chimeric modified conantokin polypeptide.

According to some embodiments, the chimeric polypeptide includes a modified conantokin peptide amino acid sequence positioned towards the N-terminus of the chimeric polypeptide and a transmembrane domain amino acid sequence positioned towards the C-terminus of the chimeric polypeptide.

According to some embodiments, there is provided a host cell including the chimeric polypeptide. In some embodiments, the host cell may be in-vitro or in-vivo.

According to some embodiments, there is provided a method of producing the modified polypeptides disclosed herein, the method includes the steps of: (i) culturing host cells under conditions such that the modified peptide or the chimeric polypeptide comprising the same is expressed; and (ii) optionally recovering the modified peptide or chimeric polypeptide from the host cells or from the culture medium.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-B—Cartoon depiction of spatial expression of a chimeric modified Conantokin polypeptide in neuronal cells. FIG. 1A—depiction of synaptic and extrasynaptic region, NMDAR and spatial expression of a chimeric modified Con-peptide; FIG. 1B depiction of neuronal cells whereby only specific, selected cells (degeneration prone neurons) express the chimeric modified Conantokin polypeptide;

FIG. 2—schematic representation of portions of nucleic acids molecules encoding for chimeric modified Con polypeptide, according to some embodiments;

FIGS. 4A-F—graphs showing the activity of NMDAR subunits expressed in *Xenopus* oocytes in the presence of increasing amounts of native Con-G (FIGS. 4A-B), or modified Con-G (FIGS. 4D-E);

FIGS. 4C and 4F show Dose-response curves of the native Con-G, and the naked Con-G, respectively;

FIG. 5A-G—graphs showing the traces of GluN2B subtype NMDAR subunits response in the presence of native Con-G or naked Con-G in a low and saturating concentration of glutamate, in *Xenopus* oocytes, as recorded by two-electrode voltage clamp (FIGS. 5A and 5B). FIG. 5C shows comparison between Native and Naked Con-G competitiveness. FIGS. 5D and 5E show traces of voltage-gradient responses of GluN2B expressed in oocytes, pre and post treatment with either Native or Naked Con-G. FIGS. 5F and 5G show Current-Voltage curves summary. Black and color (originally) horizontal bars represent agonists and toxin application, respectively. ***P<0.001;

FIG. 6A shows graphs of GluN2A/B subtypes responses to a variety of modified Con-G peptides (sequences of which are detailed in Table 1); FIG. 6B and FIG. 6C show graphs of are trace and summary, respectively, of GluN2B subtype response to a high concentration of scrambled Naked Con-G control peptide (SEQ ID NO: 15); FIG. 6D and FIG. 6E show graphs of the trace and summary, respectively, of GluN2B subtype response to increasing concentrations of alanine-substituted Con-G peptide (SEQ ID NO: 12); FIG. 6F and FIG. 6G show graphs of the trace and summary, respectively, of GluA1/2 AMPAR response to Naked Con-G. Cyclothiazide (CTZ) was used for preventing AMPAR desensitization. Black and grey horizontal bars represent agonists and toxin application, respectively;

FIG. 7B shows a summary of the spontaneous EPSCs (sEPSC) amplitude; FIG. 7C shows Summary of spontaneous EPSCs frequency, in the presence of modified Con-G or native Con-G peptide. grey bar-CNQX 10 μM, Bicuculline 10 μM, QX-314;

FIG. 10A shows graphs of traces of GluN2B NMDA subtypes response to Con-P on GluN2B (NR2B) containing NMDARs; FIG. 10B shows graphs of traces of GluN2A (NR2A) containing NMDARs subtypes response to Con-P; FIG. 10C presents dose response curves of the effect of Con-P on activity of NR2B and NR2A containing NMDARs;

FIG. 11A—shows representative recording of NMDAR-dependent EPSCs, before and after application of naked con-P, in young or mature neurons. FIG. 11B shows averaged EPSCS before, during and after treatment (ifenprodil—grey; naked con-P- (originally) cyan). Entire expt. CNQX 10 μM, Bicuculline 10 μM, QX-314 (intra solution); FIGS. 11C-D show graphs summarizing the results of normalized inhibition (sESPC peak amplitude (FIG. 11C) and sEPSC frequency (FIG. 11D));

FIG. 14A shows a Cartoon representation of a membrane-associated modified Con-G chimeric polypeptide, illustrating the membrane-associated modified Con-G moiety, and the membranal NMDAR subunits; FIG. 14B shows Micro-graph images showing the membranal expression of the modified con-G polypeptide, as determined by fluorescence imaging of the fluorescent marker (dsRed); FIG. 14C shows Glutamate dose-response curves for GluN1a/GluN2B receptors expressed in HEK293 cells, with (right) or without (left) the membranal modified-Con-G polypeptide; FIG. 14D-FIG. 14E shows summarizing graphs representing the Maximal current compared between groups with (white bars) or without (black bars) co-expression of the membranal modi-fied-Con-G polypeptide (pA/pF) (n=10);

FIG. 15A shows pictograms of the expression of a modi-fied Con-P in HEK cell membrane, as determined by detection of the C-Myc tag (Green), ds-Red fluorescent signal (red emitted from the fluorescent protein marker) and DAPI staining of the cells' nucleus; FIG. 15B, shows pictograms of the expression of the modified Con-P with or without expression of GluN2B receptor subunit (left hand panel). The expression results are quantitated and presented in in the graphs on the right hand panel of FIG. 15B.

DETAILED DESCRIPTION OF THE INVENTION

Figure 3A:
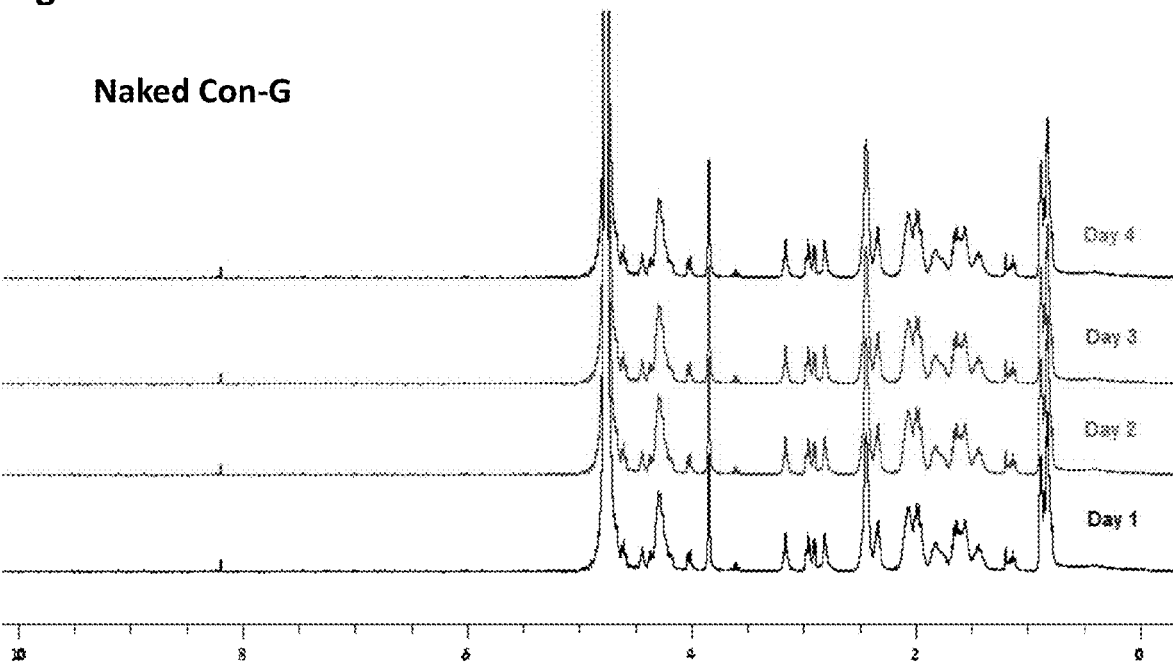
FIGS. 3A-B—Graphs showing the stability of naked Con-G (FIG. 3A) and naked Con-P (FIG. 3B) at room temperature, over a time period of four days, as determined by NMR.

The principles, uses, and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "polynucleotide molecules", "oligonucleotide", "polynucleotide", "nucleic acid" and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded (ss), double stranded (ds), triple stranded (ts), or hybrids thereof. The polynucleotides may be, for example, or polynucleotide sequences of DNA or RNA. The DNA or RNA molecules may be, for example, but are not limited to: complementary DNA (cDNA), genomic DNA, synthesized DNA, recombinant DNA, or a hybrid thereof or an RNA molecule such as, for example, mRNA. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions. As used herein, nucleotides (A, G, C or T) and nucleotide sequences are marked in lowercase letters (a, g, c or t). In some embodiments, a nucleic acid molecule may be comprised of serval nucleotide sequences (that may be coding sequences, regulatory sequences and/or non-coding sequences). In some embodiments, the nucleic acid molecule comprised of several nucleotide sequences may also be referred to as "cassette". In some embodiments, if the nucleic acid molecule is expressed (i.e., encodes for a peptide or chimeric polypeptide to be expressed), the cassette may be termed "expression cassette".

The terms "polypeptide," "peptide" and "protein" are used interchangeably herein to refer to a polymer of amino acid residues. In some embodiments, one or more of amino acid residue in the polypeptide, can contain modification, such as but be not limited only to, glycosylation, phosphorylation or disulfide bond shape. Also provided are conservative amino acid variants of the peptides and protein molecules disclosed herein. Variants according to the invention also may be made that conserve the overall molecular structure of the encoded proteins or peptides. As used herein, Amino acids and peptide sequences are marked using conventional Amino Acid nomenclature (single letter or 3-letters code). For example, amino acid "Serine" may be marked as "Ser" or "S" and amino acid "Cysteine" may be marked as "Cys" or "C". In some embodiments, a peptide refers to a short (for example, 12-25) amino acid sequences. In some embodiments, a polypeptide refers to a longer stretch of amino acids, which is comprised of a chimera of at least two distinct peptides expressed as one polypeptide (for example, a modified conantokin related peptide and a protein tag).

As referred to herein, the term "complementarity" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A or a) forms a base pair with thymine (T or t) and guanine (G or g) with cytosine (C or c). In RNA, thymine is replaced by uracil (U or u). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

The term "construct", as used herein refers to an artificially assembled or isolated nucleic acid molecule which may be comprises of one or more nucleic acid sequences, wherein the nucleic acid sequences may be coding sequences (that is, sequence which encodes for an end product), regulatory sequences, non-coding sequences (for example, linkers), or any combination thereof The term construct includes, for example, vectors, plasmids but should not be seen as being limited thereto. The term "regulatory sequence" in some embodiments, refers to DNA sequences, which are necessary to affect the expression of coding sequences to which they are operably linked (connected/ligated). The nature of the regulatory sequences differs depending on the host cells. For example, in prokaryotes, regulatory/control sequences may include promoter, ribosomal binding site, and/or terminators. For example, in eukaryotes regulatory/control sequences may include promoters (for example, constitutive, inducible and/or tissue or cell specific), terminators, enhancers, transactivators and/or transcription factors. A regulatory sequence which is "operably linked" to a coding sequence is ligated in such a way that expression of the coding sequence is achieved under suitable conditions. In some embodiments, a "Construct" or a "DNA construct" refer to an artificially assembled or isolated nucleic acid molecule which comprises a coding region of interest (for example, encoding the modified con peptide) and optionally additional regulatory and/or non-coding sequences.

As used herein, the term "vector" refers to any recombinant polynucleotide construct (such as a DNA construct) that may be used for the purpose of transformation, i.e., the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced. The term "Expression vector" refers to vectors that have the ability to incorporate and express heterologous nucleic acid fragments (such as DNA) in a foreign cell. In other words, an expression vector comprises nucleic acid sequences/fragments (such as DNA, mRNA), capable of being transcribed or expressed in a target cell. Many viral, prokaryotic and eukaryotic expression vectors are known and/or commercially available. Selection of appropriate expression vectors is within the knowledge of those having skill in the art. The expression vectors can include one or more regulatory sequences. In some embodiments, a vector is a viral vector, such as, for example, adeno-virus (AVV) associated virus.

As used herein, the term "transformation" refers to the introduction of foreign DNA into cells. The terms "transformants" or "transformed cells" include the primary transformed cell and cultures derived from that cell regardless to the number of transfers. All progeny may not be precisely identical in DNA content, due to deliberate or inadvertent mutations. Mutant progeny that has the same functionality as screened for in the originally transformed cell are included in the definition of transformants.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, injection, and the like, or combinations thereof. The transfection of the cell may be performed on any type of cell, of any origin, such as, for example, human cells, animal cells, plant cells, and the like. The cells may be isolated cells, tissue cultured cells, cell lines, cells present within an organism body, and the like.

The terms "upstream" and "downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

As used herein, the term "treating" includes, but is not limited to one or more of the following: abrogating, ameliorating, inhibiting, attenuating, blocking, suppressing, reducing, delaying, halting, alleviating or preventing symptoms associated with a condition. Each possibility represents a separate embodiment of the present invention. In some embodiments, the condition is a neurodegenerative condition. In some exemplary embodiments, the condition may be selected from, Alzheimer's disease (AD), Parkinson's diseases (PD), Amyotrophic lateral sclerosis (ALS), traumatic brain injury (TBI), Huntington's Disease (HD), and the like, or combinations thereof.

The term "modulating", as used herein refers to affecting the activity of a receptor, such as, NMDA receptor, GABA receptor, and the like. In some embodiments, modulation relates to affecting activity or function of a subunit of a receptor, such as, NMDA receptor. For example, modulation may include reducing (inhibiting, preventing) activity of the receptor (or specific subunit thereof). For example, modulation may include increasing (elevating) activity of the receptor (or specific subunit thereof).

As used herein, the terms "conantokin peptide", "Con peptide" and "Conatoxin" may interchangeably be used. The terms relate to a naturally occurring ("native") peptide found or isolated from the *Conus* Species. As is known in the art each of the Con peptides include two or more several gamma-carboxyglutamyl ("y-carboxyglutamyl", "Gla" or "GLA") residues. Further, it is to be understood that con peptide is interchangeable with any alternative name or synonym of this protein known in the art. The con-peptides include, for example, any of the subtypes, Con-G, Con-P, Con-Pr3, Con-T, Con-R, con-E, Con-L, Con-Pr1, Con-Pr2, Con-Br and/or Con-RIA. For example, the amino acid sequence of naturally occurring Con-P is denoted by SEQ ID NO: 1. For example, the amino acid sequence of naturally occurring Con-G is denoted by SEQ ID NO: 2. For example, the amino acid sequence of naturally occurring Con-Pr3 is denoted by SEQ ID NO: 3.

As used herein, the term "modified conantokin peptide" relates to an artificial, non-naturally occurring peptide having at least one amino acid modification as compared to a corresponding WT, naturally occurring Con peptide. In some embodiments, the term also relates to a peptide having similarity to a naturally occurring Con peptide, for example, a peptide derived from APP protein. In some embodiments, the amino acid modification may include any type of modification, including, substitution, replacement, deletion and/ or addition of one or more amino acids. In some embodiments, the term modification relates to substitution of an amino acid residue. In some embodiments, the modification may include replacement of one or more of the GLA residues of a naturally occurring con peptide. In some embodiments, one or more additional amino acids (in addition to the GLA) may also be replaced in the modified con peptide. In some embodiments, the modification may include replacement of at least two GLA residues of a naturally occurring con peptide. In some embodiments, the modification may include replacement of at least three GLA residues of a naturally occurring con peptide. In some embodiments, the modification may include replacement of at least four GLA residues of a naturally occurring con peptide. In some embodiments, the modification may include replacement of at least five GLA residues of a naturally occurring con peptide. In some embodiments, the modification may include replacement of GLA with one or more of: Glutamate (E), Asp (D), Alanine (A) and/or Glycine (G). In some embodiments, a modified peptide may include substitution of all GLA residues of the respective naturally occurring Con peptide. In some embodiments, all substitutions are with the same residue (for example, replacement of GLA with E, D, A or G). In some embodiments, the substitutions may be with a variety of amino acids (for example, one GLA is replaced with E and the other is replaced with D). In some embodiments, as used herein, a modified con peptide, in which all GLA of the corresponding WT con peptide have been replaced with Glutamate is referred to herein, as "naked con peptide". For example, a "naked con-P" (SEQ ID NO: 4) is a modified Con-P peptide in which all five GLA residues of the naturally occurring Con-P peptides are replaced with Glutamate. For example, a "naked con-G" (SEQ ID NO: 8) is a modified Con-G peptide having all five GLA residues of the naturally occurring Con-G peptides replaced with Glutamate. For example, a "naked con-Pr3" (SEQ ID NO: 13) is a modified Con-Pr3 peptide having all GLA residues of the naturally occurring Con-G peptides replaced with Glutamate. In other example, a modified con peptide may be a con-related peptide, which is a protein having at least some similarity to a con peptide. In some embodiments, as detailed below, such peptide is an Amyloid-Precursor-Protein (APP) derived peptide (also referred to herein as "cAPP"), having an amino acid sequence as denoted by SEQ ID NO: 14. cAPP is a short sequence at the extracellular domain of APP (not Aβ) that exhibits the signature sequence of con peptides, namely negative charges at N-terminus (NT).

In some embodiments, a modified con peptide is an isolated peptide. In some embodiments, a modified conantokin peptide is non-naturally occurring (i.e., when expressed in a host or target cells, it is different than a corresponding conantokin peptide which is expressed in an authentic, *Conus* cell). According to some embodiments, the modified con peptide is soluble. In some embodiments, the modified con peptide is in the form of a chimeric polypeptide, harbored or expressed in the target or host cell. In some embodiments, the chimeric polypeptide is spatially and/or temporally expressed. In some embodiments, the chimeric polypeptide is attached or associated with a cell membrane. In some embodiments, the chimeric polypeptide includes a transmembrane domain (TMD). According to some embodiments, a modified con peptide is a recombinant protein, polypeptide or peptide. As used herein, the term "isolated" means it is not occurring in nature.

In some embodiments, the modified peptides/chimeric polypeptides and/or nucleic acids encoding the same, as disclosed herein, may be expressed or harbored in a host or target cell. The terms "host cell" and "target cell" may interchangeably be used. The terms relate to a viable cell harboring or expressing the nucleic acid molecules and/or modified Con peptides. In some embodiments, the host cell is a vertebrate cell. In some embodiments, the host cell is a mammalian cell. In some embodiments, the host cell is a human cell. In some embodiments, the host cell is a neuronal cell. In some embodiments, the host cell has, forms or involves a synapse. In some embodiments, the host cell is capable of expressing or being affected by a neurotransmitter. In some embodiments, the host cell expresses NMDA receptor. In some embodiments, the NMDA receptor may include GluN2B subunit, GluN2A subunit, or both. In some embodiments, the host cell is in vitro (i.e., not within an organism). In some embodiments, the host cell is in-vivo (e.g., within an organism or a tissue).

According to some embodiments, as exemplified herein, the modified peptides disclosed herein (such as, modified Con-G peptides, modified Con-P peptides, modified Con-Pr3 peptides and/or APP related peptides) are capable of blocking NMDAR currents of NMDARs expressed in *Xenopus* Laevis oocytes, as determined using two-electrode voltage clamp. In some embodiments, such modified peptides have no effect on a-amino-3-hydroxy-5-methyl-4-isoxazole-propionic acid receptors (AMPARs), which are another type of glutamatergic receptor found in excitatory synapses. In some embodiments, at least some of the modified peptides are able to potentiate GABAbR. In some embodiments, when the modified peptides are tested on rat hippocampal neurons, activity-monitoring of neurons (action potential firing) via calcium imaging revealed a robust inhibition of activity, which was reversable upon wash of the modified peptides.

In some embodiments, as exemplified herein, modified con-G and cAPP inhibit NMDAR and activate/potentiate GABAbRs to collectively inhibit ex-GluN2B-receptor, reduce Ca2+-overload and promote suppression of neuronal hyperexcitability; ultimately leading to rescue of neurons in a diseased brain.

In some embodiments, there is provided a nucleic acid molecule encoding a modified con peptide comprising an amino acid sequence of a modified Con peptide, wherein at least one GLA residue found in the naturally occurring con peptide is replaced by a different amino acid residue (selected, for example, from: alanine, Aspartate, Glycine and Glutamate).

In some embodiments, the modified con peptide is a modified Con-P peptide. In some embodiments, the modified Con-P peptide may have an amino acid sequence as denoted by any one of exemplary SEQ ID NOs: 4-7. Each possibility is a separate embodiment. For example, the modified Con-P may be a "naked" con-P having an amino acid sequence as denoted by SEQ ID NO: 4. For example, the modified Con-P may be an Alanine-substituted ("Ala-Sub" con-P having an amino acid sequence as denoted by SEQ ID NO: 5. For example, the modified Con-P may be an Aspartate-substituted ("Asp-Sub" con-P having an amino acid sequence as denoted by SEQ ID NO: 6. For example, the modified Con-P may be a Glycine-substituted ("Gly-Sub" con-P having an amino acid sequence as denoted by SEQ ID NO: 7. In some embodiments, at least one of the GLA amino acids found in a naturally occurring Con-P peptide (Represented by SEQ ID NO: 1) may be replaced or substituted by another amino acid, such as, for example, Glutamate, Glycine, Alanine or Aspartate. In some embodiments, at least one, at least two, at least three, at least four or all five of the GLA amino acids found in a naturally occurring Con-P peptide (Represented by SEQ ID NO: 1) may be replaced or substituted by another amino acid. In some embodiments, the GLA may be replaced by the same or different amino acid. In some embodiments, further amino acids of the naturally occurring Con-P peptide may be replaced by another amino acid. For example, Glutamate may be replaced, for example, by Aspartate. It is to be understood that various amino acids substitutions or a combination of such substitutions are contemplated under the scope of this disclosure, and the specific amino acid sequences of the modified Con-P peptides are exemplary.

According to some embodiments, there are provided nucleic acid molecules encoding for the modified Con-P peptides disclosed herein. In some embodiments, the nucleic acid molecules encoding for the modified Con-P peptides have a nucleic acid sequence as denoted by any one of exemplary SEQ ID NOs: 17-20.

According to some embodiments, as exemplified herein, surprisingly and unexpectedly, it was shown that modified Con-P peptides (such as, naked Con-P, or other modified Con-P peptides) not only remain functional in inhibiting GluN2B-receptors, they can also robustly act as potentiator of GluN2A-receptors in mammalian cells (such as, HEK293t cells) as well as in neurons. Thus, according to some embodiments, such modified con-P peptides as disclosed herein are powerful synaptic-enhancers that can be utilized for enhancing cognitive abilities and treating neurodegenerative conditions.

In some embodiments, the modified Con peptide is a modified Con-G peptide. In some embodiments, the modified Con-G peptide may have an amino acid sequence as denoted by any one of exemplary SEQ ID NOs: 8-12. Each possibility is a separate embodiment. For example, the modified Con-G may be a "naked" con-G having an amino acid sequence as denoted by SEQ ID NO: 8. For example, the modified Con-G may be an E7A substituted naked Con-P ("Naked con-G E7A") having an amino acid sequence as denoted by SEQ ID NO: 9. For example, the modified Con-G may be a truncated naked Con-G ("Naked Con-G 1-13") having an amino acid sequence as denoted by SEQ ID NO: 10. For example, the modified Con-G may be an E7A substituted and truncated naked Con-G ("S. (short) Naked Con-G 1-13") having an amino acid sequence as denoted by SEQ ID NO: 11. For example, the modified Con-G may be an Alanine-substituted ("Ala-Sub") con-G having an amino acid sequence as denoted by SEQ ID NO: 12. In some embodiments, at least one of the GLA amino acids found in a naturally occurring Con-G peptide (Represented by SEQ ID NO: 2) may be replaced or substituted by another amino acid, such as, for example, Glutamate, Glycine, Alanine or Aspartate. In some embodiments, at least one, at least two, at least three, at least four or all five of the GLA amino acids found in a naturally occurring Con-G peptide (SEQ ID NO: 2) may be replaced or substituted by another amino acid. In some embodiments, the GLA may be replaced by the same or different amino acid. In some embodiments, further amino acids of the naturally occurring Con-G peptide may be replaced by another amino acid. For example, Glutamate may be replaced, for example, by Aspartate. It is to be understood that various amino acids substitutions or a combination of such substitutions are contemplated under the scope of this disclosure, and the specific amino acid sequences of the modified Con-G peptides are exemplary.

According to some embodiments, there are provided nucleic acid molecules encoding for the modified Con-G peptides disclosed herein. In some embodiments, the nucleic acid molecules encoding for the modified Con-G peptides have a nucleic acid sequence as denoted by any one of exemplary SEQ ID NOs: 21-25.

In some embodiments, the modified Con peptide is a modified Con-Pr3 peptide. In some embodiments, the modified Con-Pr3 peptide may have an amino acid sequence as denoted by exemplary SEQ ID NOs: 13 ("naked" con-Pr3). In some embodiments, at least one of the GLA amino acids found in a naturally occurring Con-Pr3 peptide (Represented by SEQ ID NO: 3) may be replaced or substituted by another amino acid, such as, for example, Glutamate, Glycine, Alanine or Aspartate. In some embodiments, at least one, at least two, or all three, GLA amino acids found in a naturally occurring Con-Pr3 peptide (SEQ ID NO: 3) may be replaced or substituted by another amino acid. In some embodiments, the GLA may be replaced by the same or different amino acid. In some embodiments, further amino acids of the naturally occurring Con-Pr3 peptide may be replaced by another amino acid. For example, Glutamate may be replaced, for example, by Aspartate. It is to be understood that various amino acids substitutions or a combination of such substitutions are contemplated under the scope of this disclosure, and the specific amino acid sequences of the modified Con-Pr3 peptides are exemplary. According to some embodiments, there are provided nucleic acid molecules encoding for the modified Con-Pr3 peptides disclosed herein. In some embodiments, the nucleic acid molecules encoding for the modified Con-Pr3 peptides have a nucleic acid sequence as denoted by exemplary SEQ ID NO: 26.

According to some embodiments, the modified Con peptide is a peptide related to a Con-G peptide, by sequence similarity. In some embodiments, such related peptide is a peptide derived from the mammalian APP protein. In some embodiments, the APP related protein is a Con-G like APP ("cAPP) having an amino acid sequence as denoted by SEQ ID NO: 14. In some embodiments, the APP related protein is an APP long peptide (17AA, "17-mer") having an amino acid sequence as denoted by SEQ ID NO: 43. In some embodiments, the APP related protein is a short APP peptide having an amino acid sequence as denoted by SEQ ID NO: 44.

According to some embodiments, as exemplified herein, the Conantokin-like sequence found within the sequence of the mammalian Amyloid-Precursor-Protein ("cAPP") can inhibit NMDAR-currents in a dose-dependent manner akin to the modified con peptides (for example, the naked peptides). Furthermore, surprisingly, the naked con-G peptide, cAPP and 17-mer APP can directly activate GABAb receptors.

According to some embodiments, the modified Con peptides disclosed herein may be administered as soluble proteins (as is, or in a suitable composition), to exert a biological effect, as detailed below.

According to some embodiments, by use of two-electrode and whole-cell patch clamp recordings and heterologous expression of NMDA receptors in *Xenopus* oocytes and Human Embryonic Kidney 293 (HEK293) cells, the functionality and selectivity of the modified Con-peptides, can be assessed. Further, in some embodiments, the modified Con-peptides can also be employed on cultured neurons, where their ability to inhibit endogenous NMDARs as well as other parameters such as resting potential, intrinsic excitability and firing rate can be determined. In some embodiments, the effect of the modified Con-peptides on synaptic and extrasynaptic Ca2+-activity can be performed by imaging Ca2+-activity in dendrites and spines with genetically-encoded calcium indicators (GECIs) and confocal microscopy tools.

According to some embodiments, the modified Con-peptides disclosed herein may be expressed as chimeric polypeptide with one or more additional protein/peptide moieties, to allow a desired temporal and/or spatial expression thereof in target cells. In some embodiments, as detailed herein, the target cells can be vertebrate cells, for example, neurons, and the spatial expression may be in presynaptic or extrasynaptic regions, for example, by being attached to or associated with the cell membrane. In some embodiments, as detailed herein, the spatial expression may be in specific cells (such, for example, diseased cells). In some embodiments, as detailed herein, a temporal expression may be at specific timing during the activation of the cells, or according to the cell condition (for example, in apoptotic cells).

Reference is now made to FIGS. 1A-B, which are cartoon representations of spatial expression of a chimeric modified Conantokin polypeptide in neuronal cells. As shown in FIG. 1A, when synaptic glutamate (2) spillover (marked by dashed arrow) to extrasynaptic locations (4) occurs, this leads to excessive activation of ex-GluN2B receptors (6), excessive Ca2+-entry and neuronal death. A spatially confined chimeric modified Con-peptide (8) that can selectively inhibit ex-GluN2B receptors, would in turn, negate degeneration. Reference is now made to FIG. 1B further demonstrating a spatio-temporal expression of chimeric modified Conantokin polypeptide, whereby only degeneration prone neurons (expressing specific proteins/markers) express the modified Con-peptide (for example by utilizing tissue specific promoters, as detailed herein). Thus, targeting expression of the t-toxin to selected neurons, particularly degeneration-prone neurons (20), thereby leaving other neurons (and their NMDARs, whether synaptic or extrasynaptic) unperturbed, thereby minimizing side-effects.

According to some embodiments, there is thus provided a nucleic acid molecule encoding a polypeptide comprising an amino acid sequence of a modified con peptide, as disclosed herein, wherein at least one GLA residue found in naturally occurring con peptide is replaced by a different amino acid residue (selected, for example, from alanine, Aspartate, Glycine and Glutamate) and at least one additional protein moiety, selected from, but not limited to: a signal peptide, a transmembrane domain, a protein tag, a fluorescent protein, or any combination thereof. In some embodiments, such nucleic acid molecule may further include one or more regulatory sequences (such as, an inducible promoter, constitutive promoter or a tissue specific promoter), which are operably linked to the coding sequences (of the modified con peptide and/or any of the other protein moieties).

According to some embodiments, there is thus provided a nucleic acid molecule for expressing a chimeric modified conantokin polypeptide in or on a membrane of a target cell, the nucleic acid molecule includes: a first nucleotide sequence encoding for a modified conantokin peptide, such as, modified Con-P, modified Con-G, modified Con-Pr3, or a Con-related peptides, such as cAPP; a second nucleotide sequence encoding for a transmembrane domain, capable of directing the expressed modified peptide to the membrane, wherein, in some embodiments, the second nucleotide sequence is located downstream of the first nucleotide sequence; and a third nucleotide sequence, being a regulatory sequence capable of affecting expression of the modi-
fied conantokin peptide within the target cell, for example,
by imparting a temporal and/or spatial expression thereof.

Reference is now made to FIG. 2, which show schematic
arrangements of portions of nucleic acids molecules encod-
ing for chimeric modified Con polypeptide, according to
some embodiments. As shown in FIG. 2, exemplary nucleic
acid molecules may include such exemplary regions as, but
not limited to: signal peptide coding region ("Sig. pep."),
modified Com-peptide coding region ("toxin"), a protein tag
coding region ("tag"), a linker (short linker ("S-linker") or
long linker ("L-linker") region, a transmembrane domain
coding region ("TMD"), and a second protein marker
("Flou. Marker"), or any combination thereof. The order/
orientation of the regions may be as depicted in FIG. 2, or
in any other suitable desired order. In some embodiments,
the nucleic acid molecules may further include a dedicated
promoter that can allow controlling the expression of the
chimeric modified Con-peptides. Depending on the purpose
and the intended expression of the chimeric polypeptide
encoded by the nucleic acid molecule, such promoter may be
a constitutive promoter, an inducible promoter, a tissue
specific promoter or a promoter activated under specific
cellular conditions (for example, apoptosis or neurodegen-
eration).

In some embodiments, the nucleic acid molecule encod-
ing for the modified con chimeric polypeptide disclosed
herein is preferably at least 50% homologous/identical to the
nucleic acid sequence of the nucleic acid molecules of a
naturally occurring con peptide. It is understood that such
nucleic acid sequences can also include orthologous/ho-
mologous/identical (and thus related) sequences. More pref-
erably, the nucleic acid sequence encoding the provided
modified con peptides is at least 52%, 53%, 55%, 60%, 65%,
70%, 75%, 80%, 85%, 90%, 91%, 92%, 93%, 94%, 95%,
96%, 97%, 98%, or 99% homologous/identical to the
nucleic acid sequence as shown in SEQ ID NO: 17-27,
wherein the higher values of sequence identity are preferred.

According to some embodiments, as detailed herein, the
modified conantokin chimeric polypeptide may include a
protein tag. As used herein, the term "protein tag" refers to
a peptide sequence bound to or in closer to the N-terminus
or C-terminus of the peptide. According to some embodi-
ments, the protein tag may comprise a glycoprotein. Accord-
ing to some embodiments, the protein tag may be used for
separation, purification and/or identification/tracking of the
tagged protein. Non-limiting examples of protein tags
include: Myc-Tag, Human influenza hemaglutinin (HA),
Flag-Tag, His-Tag, Gluthathione-S-Transferase (GST) and a
combination thereof. Each possibility represents a separate
embodiment of the present invention. In some exemplary
embodiments, the tag is a Myc-tag, having an amino acid
sequence as denoted by SEQ ID NO: 31 (encoded by a
nucleic acid molecule having a nucleotide sequence denoted
by SEQ ID NO: 32).

According to some embodiments, the modified con chi-
meric polypeptide may include a protein tag upon produc-
tion, which may be consequently cleaved and/or removed
from modified peptide prior to incorporation into a compo-
sition or prior to being introduced/administered to cells.
Cleavage and/or removal of a tag may be performed by any
method known in the art, such as, but not limited to,
enzymatic and/or chemical cleaving.

According to some embodiments, as detailed herein, the
modified conantokin chimeric polypeptide may further
include a fluorescent protein tag. The fluorescent protein tag
may be found on or be closer to the C-terminus or N-terminus of the peptide. In some embodiments, the fluorescent
protein tag may be selected from, but not limited to: Azurite,
TagBFP, mTagBFP, mTagBFP2, Cerulean, ECFP, TagCFP,
AmCyan, T-Sapphire, LSS-mKate1, LSS-mKate2, Tur-
boGFP, EGFP, TagGFP, Emerald GFP, TagYFP, TurboYFP,
EYFP, Topaz, Venus, Citrine, mKOm, mOrange, mOrange2,
Kusabira Green Orange, E2 Orange, DsRed, DsRed2,
DsRed-Express, tdTomato, TagRFP, mStrawberry, mCherry,
mKate, mKate2, TurboFP635, mPlum, HcRed, mRaspberry,
mNeptune, E2Crimson, or combinations thereof. Each pos-
sibility is a separate embodiment.

According to some embodiments, as detailed herein, the
modified conantokin chimeric polypeptide may further
include a linker region. The linker region may be introduced
between any of the protein moieties of the chimeric poly-
peptide. For example, the linker may be placed between a
protein tag and the modified peptide amino acid sequences.
For example, a linker may be placed between a modified
amino peptide amino acid sequence and a fluorescent protein
sequence. In some embodiments, the linker may be short
(for example, in the range of about 5-15 amino acids). In
some embodiments, the linker region may be long. In some
exemplary embodiments, a short linker region may have an
amino acid sequence as denoted by SEQ ID NO: 35 (en-
coded by a nucleic acid molecule having a nucleotide
sequence denoted by SEQ ID NO: 36). In some exemplary
embodiments, a long linker region may have an amino acid
sequence as denoted by SEQ ID NO: 33 (encoded by a
nucleic acid molecule having a nucleotide sequence denoted
by SEQ ID NO: 34).

According to some embodiments, as detailed herein, the
modified conantokin chimeric polypeptide may further
include a signal peptide region. The signal region may be
introduced between any of the protein moieties of the
chimeric polypeptide. For example, the signal peptide may
be placed at the N-terminus of the chimeric polypeptide. In
some embodiments, the signal peptide may be any suitable
signal peptide known in the art. In some embodiments, a
signal peptide (also referred to as "signal sequence", "tar-
geting signal", "localization signal") is a short peptide
(about 10-30 amino acids long) which can direct the form
polypeptide toward the secretory pathway, to affect their
cellular localization. In some embodiments, the signal pep-
tide is a membrane insertion signal. In some exemplary
embodiments, the signal peptide may have an amino acid
sequence as denoted by SEQ ID NO: 29 (encoded by a
nucleic acid molecule having a nucleotide sequence denoted
by SEQ ID NO: 30).

According to some embodiments, as detailed herein, the
modified conantokin chimeric polypeptide may further
include a transmembrane domain (TMD). TMDs in the form
of a-helical domains are found in most integral membrane
proteins that span the hydrophobic core of the lipid bilayer.
TMD can direct the expressed modified peptide to the cell
membrane. According to some embodiments, utilizing a
TMD to direct the expressed chimeric polypeptide to the
membrane is advantageous over the use of other membrane
tethering moieties, such as, Glycosylphosphatidylinositol
(GPI). In some embodiments, the TMD is of PDGF receptor.
In some exemplary embodiments, the TMD may have an
amino acid sequence as denoted by SEQ ID NO: 37 (en-
coded by a nucleic acid molecule having a nucleotide
sequence denoted by SEQ ID NO: 38).

According to some embodiments, as detailed herein, the
modified conantokin chimeric polypeptide may further
include one or more additional sequences/motifs, such as,
for example, but not limited to: a trafficking motif ERXL (which is a fusion peptide of the trafficking and ER export signals from Kir2.1), an ER-export signal, and/or a Golgi-export motif/signal. In some exemplary embodiments, the ERXL trafficking motif may have an amino acid sequence as denoted by SEQ ID NO: 47 (encoded by a nucleic acid sequence as denoted by SEQ ID NO: 48). In some exemplary embodiments, the ER-export signal may have an amino acid sequence as denoted by SEQ ID NO: 45, encoded by a nucleic acid sequence as denoted by SEQ ID NO: 39). In some exemplary embodiments, the Golgi-export motif (also referred to herein as "SWTY") may have an amino acid sequence as denoted SEQ ID NO: 4 6, encoded by a nucleic acid sequence as denoted by SEQ ID NO: 40).

According to some embodiments, as detailed herein, the nucleic acid encoding for the modified conantokin chimeric polypeptide may further include a regulatory sequence, configured to allow control over the spatial and/or temporal expression of the polypeptide in target cells. In some embodiments, the regulatory element may include at least a partial promoter. The promoter may be any type of suitable promoter, including, for example, but not limited to: constitutive promoter, inducible promoter and/or tissue specific promoter. In some embodiments, the promoter may be an apoptotic promoter (i.e., a promoter which is activated only in apoptotic cells). In some embodiments, exemplary apoptotic promoters include such promoters of genes as, but not limited to: BBC3, FOXO1, CASP3, CLCA1, and the like. Each possibility is a separate embodiment. In some embodiments, the promoters may be promoters of genes that undergo selective upregulation during degeneration. In some exemplary embodiments, the promoters may be promoters of "death" genes, such as, for example, but not limited to: RASGEF1B, SLC26A3, LINGO, GNAI2, NEK6, UBE2D3, CDC42EP4, ERCC391, and the like, or any combination thereof. Each possibility is a separate embodiment. In some embodiments, the promoters may be such promoters as, but not limited to: CMV, CAG, hSyn, GFAP, and the like. Each possibility is a separate embodiment. In some exemplary embodiments, in order to restrict the expression of chimeric polypeptides (also referred to as "ex-t-Cons") to degenerating neurons only, polypeptides may be placed under the control of apoptosis/neurodegeneration-related promoters, that are turned on during initiation of the latter. These include promoters of various caspases, endonucleases and transcription factors. Importantly, these have very low basal expression under normal conditions (i.e., in healthy neurons), but are highly upregulated in degeneration processes, notably apoptosis. This would enable the expression of the chimeric membranal polypeptides when the fate of the cell has not been determined yet, i.e., apoptosis-related proteins are being engaged, but the process has not been initiated.

According to some embodiments, in order to localize the chimeric polypeptides to extrasynaptic regions the polypeptides may include intracellular tails (for example, at the carboxy-termini; CT) of extrasynaptic expressing receptors, such as, for example, mGluR1/5. Localization of the chimeric polypeptides at the extrasynapse can be discerned, for example, using imaging of synaptic sites (for example, by labeling of PSD-95) in expanded hippocampal slices. Extrasynaptic localization can also be assessed functionally by measuring synaptic and extrasynaptic NMDA-dependent EPSCs as well as functional LTP. syNMDARs are crucial for induction of Long-Term Potentiation (LTP), therefore inhibition of the latter should eliminate the ability to induce LTP by tetanic stimulation of Schaffer Collaterals. In order to isolate exNMDAR activity, synaptic activity may be facilitated (for example, by addition of 10-100 μM Glycine) and co-application of the NMDAR-selective activity-dependent channel blocker, such as, MK-801. Such protocol mostly inhibits syNMDAR activity, whilst leaving the remaining responses to exNMDARs.

According to some embodiments, in order to assess the expression and functionality of the nucleic acid molecules encoding for the chimeric polypeptides, such nucleic acid molecules may be transiently transfected into cells (such as HEK-293 cells and neuron cells). The expression and localization of the various chimeric polypeptides may then be assessed by immunostaining and imaging of fluorescent proteins. To examine functionality, the cells may be co-transfected and different subtypes of the NMDAR and the current-responses via whole-cell patch clamp is measured and their ability to inhibit GluN2B-containing receptor vs. other receptor subtypes can be compared. The fluorescence signal emitted from the chimeric polypeptides and/or the co-expressed-tagged-NMDARs can be used to establish a pseudo-dose-response curves. The effect of the chimeric polypeptides can also be tested on other members of the glutamate receptor-family, as well as on other synaptic ions channels and receptors (e.g., AMPA). In some embodiments, the chimeric polypeptides can be expressed in cultured neurons that express endogenous NMDARs subtypes, and their ability to block said receptors can be assessed. Specificity of activation can also be assessed, since, for example, hippocampal neurons mainly express GluN2A and 2B-containing receptors and these could be separated by pharmacology). In neurons, the effect of chimeric polypeptides one modulating other endogenous ion channels and receptor can be performed by assessing basic neuronal physiology (resting potentials, firing threshold and rates, endogenous currents, and the like).

According to some embodiments, the modified con peptides as disclosed herein may be produced by recombinant or chemical synthetic methods. According to some embodiments, modified peptides as disclosed herein may be produced by recombinant methods from genetically-modified host cells. Any host cell known in the art for the production of recombinant proteins may be used for the present invention. According to some embodiments, the host cell is a prokaryotic cell. Representative, non-limiting examples of appropriate prokaryotic hosts include bacterial cells, such as cells of Escherictahia coli and Bacillus subtilis. According to other embodiments, the host cell is a eukaryotic cell. According to some exemplary embodiments, the host cell is a fungal cell, such as yeast.

According to some exemplary embodiments, a coding region of interest is a coding region encoding modified con peptide.

In some embodiments, the modified con peptide may be synthesized by expressing a polynucleotide molecule encoding the modified peptide in a host cell, for example, a microorganism cell transformed with the appropriate nucleic acid molecule.

According to some embodiments, the polynucleotides encoding the modified con peptide or chimeric polypeptide may be cloned into any vector known in the art.

According to some embodiments, a method to producing a polynucleotide with a desired sequence is the use of a synthetic gene. A polynucleotide encoding a desired polypeptide may be prepared synthetically, for example using the phosphoroamidite.

According to some embodiments, the polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type.

In some embodiments, in case of a chimeric polypeptide ("fusion protein"), or a protein fused with a protein tag, different polynucleotides may be ligated to form one polynucleotide. In some embodiments, the polynucleotide encoding the modified con polypeptide, may be incorporated into a wide variety of expression vectors, which may be transformed into in a wide variety of host cells.

According to some embodiments, introduction of a polynucleotide into the host cell can be effected by well-known methods, such as chemical transformation (e.g., calcium chloride treatment), electroporation, conjugation, transduction, calcium phosphate transfection, DEAE-dextran mediated transfection, transvection, microinjection, cationic lipid-mediated transfection, scrape loading, ballistic introduction and infection. Representative, non-limiting examples of appropriate hosts include bacterial cells, such as cells of *E. coli* and *Bacillus subtilis*.

In some embodiments, the peptides or polypeptides may be expressed in any vector suitable for expression. The appropriate vector is determined according to the selected host cell. Vectors for expressing proteins in *E. coli*, for example, include, but are not limited to, pET, pK233, pT7 and lambda pSKF. Other expression vector systems are based on betagalactosidase (pEX); maltose binding protein (pMAL); and glutathione S-transferase (pGST).

According to some embodiments, selection of a host cell transformed with the desired vector may be accomplished using standard selection protocols involving growth in a selection medium which is toxic to non-transformed cells. For example, in the case of *E. coli*, it may be grown in a medium containing an antibiotic selection agent; cells transformed with the expression vector which further provides an antibiotic resistance gene, will grow in the selection medium. In some embodiments, upon transformation of a suitable host cell, and propagation under conditions appropriate for protein expression, the polypeptide may be identified in cell extracts of the transformed cells. Transformed hosts expressing the polypeptide may be identified by analyzing the proteins expressed by the host, for example, using SDS-PAGE and comparing the gel to an SDS-PAGE gel obtained from the host which was transformed with the same vector but not containing a nucleic acid sequence encoding the desired polypeptide.

According to some embodiments, the desired polypeptides which have been identified in cell extracts may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof. The polypeptides of the invention may be produced as fusion proteins, attached to an affinity purification protein tag, such as a His-tag, in order to facilitate their rapid purification.

According to some embodiments, the isolated polypeptide may be analyzed for various properties, for example, specific activity, using methods known in the art.

According to some embodiments, a modified peptide according to the present invention may also be produced by synthetic means using well known techniques, such as solid phase synthesis. Synthetic polypeptides may be produced using commercially available laboratory peptide design and synthesis kits. In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

According to some embodiments, there is provided a process for the production of a modified Con-peptide the process includes culturing/raising a suitable host cells under conditions allowing the expression of the modified Con-peptide and optionally recovering/isolating the produced polypeptide from the cell culture.

According to some embodiments, there is provided a nucleic acid encoding for the modified con-peptide peptide, or the chimeric polypeptide. In some embodiments, there is provide a DNA construct/vector (such as, an expression vector) harboring or comprising a nucleic acid encoding for the modified con-peptide or the chimeric polypeptide (optionally in addition to one or more regulatory sequences, non-coding sequences, and the like).

In some embodiments, various suitable vectors are known to those skilled in art, and the choice of which depends on the function desired. Such vectors include, for example, plasmids, cosmids, viruses, bacteriophages and other vectors. In some embodiments, the polynucleotides and/or vectors harboring the same can be reconstituted into vehicles, such as, for example, liposomes for delivery to target cells. Any cloning vector and/or expression vector known in the art may be used, depending on the purpose, the host cell, and the like. Such vectors may be used for in-vitro and/or in-vivo introduction/expression.

According to some embodiments, the encoding nucleic acid molecules and/or the vectors disclosed herein may be designed for direct introduction or for introduction via carrier, such as, liposomes, viral vectors (adenoviral, retroviral) into target cells.

According to some embodiments, there is provided a host cell harboring or expressing the modified Con peptide. In some embodiments, the host cell may be transformed/transfected with the vector of the present invention or with the nucleic acid encoding for the modified con peptide or chimeric polypeptide. In some embodiments, there is provided a host cell harboring or comprising the nucleic acid molecule of the invention. In some embodiments, the presence of at least one vector or at least one nucleic acid molecule in the host may mediate the expression of the modified con peptide or chimeric polypeptide in the cell. In some embodiments, the nucleic acid molecule or vector comprising the same, may either integrate into the genome of the host cell, or it may be maintained extrachromosomally.

According to some embodiments the nucleic acid molecules can be used alone or as part of a vector to express the modified Con peptide or chimeric polypeptide of the invention in cells, for purification and/or for therapy.

In some embodiments, the nucleic acid molecules (or vectors harboring the same) and/or the modified Con-peptide or chimeric polypeptide, can be used as a medicament (as is, or in the form of a composition, such as a pharmaceutical composition), for treating various neurodegenerative conditions.

According to some embodiments, there is provided a composition (also referred to herein as pharmaceutical composition) which includes the modified Con peptide, the nucleic acid encoding therefor, or vectors harboring the nucleic acids. Each possibility is a separate embodiment. In some embodiments, the composition may include one or more suitable excipients, according to the purpose, type and/or use of the composition. In some embodiments, excipient is a pharmaceutical excipient which may include or a pharmaceutical carrier, vehicle, buffer and/or diluent. According to some embodiments, there is provided a composition (also referred to herein as pharmaceutical composition) which includes the nucleic acid encoding the chimeric modified con polypeptide, or vectors harboring the nucleic acids. Each possibility is a separate embodiment. In some embodiments, the composition may include one or more suitable excipients, according to the purpose, type and/or use of the composition. In some embodiments, excipient is a pharmaceutical excipient which may include or a pharmaceutical carrier, vehicle, buffer and/or diluent.

In some embodiments, the compositions disclosed herein may be used as a medicament for treating various neurodegenerative conditions.

Thus, according to some embodiments, the modified-Con peptide (or chimeric polypeptide) can be used for the successful treatment of various neurodegenerative conditions, such as, AD, PD, ALS, HD, TBI, and the like.

According to some embodiments, any suitable route of administration to a subject may be used for the nucleic acid, polypeptide or the composition of the present invention, including but not limited to, local and systemic routes. Exemplary suitable routes of administration include, but are not limited to: orally, intra-nasally, parenterally, intravenously, topically, enema or by inhalation. According to another embodiment, systemic administration of the composition is via an injection. For administration via injection, the composition may be formulated in an aqueous solution, for example in a physiologically compatible buffer including, but not limited, to Hank's solution, Ringer's solution, or physiological salt buffer. Formulations for injection may be presented in unit dosage forms, for example, in ampoules, or in multi-dose containers with, optionally, an added preservative.

According to another embodiment, administration systemically is through a parenteral route. According to some embodiments, parenteral administration is administration intravenously, intra-arterially, intramuscularly, intraperitoneally, intradermally, intravitreally, or subcutaneously. Each of the abovementioned administration routes represents a separate embodiment of the present invention. According to another embodiment, parenteral administration is performed by bolus injection. According to another embodiment, parenteral administration is performed by continuous infusion. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art.

The preferred mode of administration will depend upon the particular indication being treated and will be apparent to one of skill in the art.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to another embodiment, administration systemically is through an enteral route. According to another embodiment, administration through an enteral route is buccal administration. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

According to some embodiments, suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

In some embodiments, if desired, disintegrating agents, such as cross-linked polyvinyl pyrrolidone, agar, or alginic acid or a salt thereof, such as sodium alginate, may be added. Capsules and cartridges of, for example, gelatin, for use in a dispenser may be formulated containing a powder mix of the composition of the invention and a suitable powder base, such as lactose or starch.

According to some embodiments, solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

In some embodiments, liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

According to some embodiments, the administration may include any suitable administration regime, depending, inter alia, on the medical condition, patient characteristics, administration route, and the like. In some embodiments, administration may include administration twice daily, every day, every other day, every third day, every fourth day, every fifth day, once a week, once every second week, once every third week, once every month, and the like.

According to some embodiments, the modified Con-peptide, the chimeric polypeptide, the nucleic acids encoding the same, and/or the compositions comprising the polypeptide or the nucleic acid molecules, when used for used for treating a neurodegenerative condition may be used in combination with other therapeutic agents. The components of such combinations may be administered sequentially or simultaneously/concomitantly in separate or combined pharmaceutical formulations by any suitable administration route.

According to some embodiments, there is provided a method of treating neurodegenerative condition, the method includes administration to a subject in need thereof a therapeutically effective amount of modified Con-peptide, such as, Con-P, as detailed herein. In some embodiments, the modified con-peptide may be administered as a polypeptide as is, or in a suitable pharmaceutical composition. In some embodiments, the modified Con-peptide may be administered as a polynucleotide encoding for the polypeptide as is, or in a suitable pharmaceutical composition.

According to some embodiments, there is provided a method of treating a neurodegenerative condition, the method includes administration to a subject in need thereof a therapeutically effective amount of a modified Con-related peptide, such as, cAPP, as detailed herein. In some embodiments, the cAPP may be administered as a polypeptide as is, or in a suitable pharmaceutical composition. In some embodiments, the cAPP peptide may be administered as a polynucleotide encoding for the polypeptide as is, or in a suitable pharmaceutical composition.

According to some embodiments, there is provided a method of treating a neurodegenerative condition, the method includes administration to a subject in need thereof a therapeutically effective amount of a chimeric modified Con-peptide, such as, chimeric modified Con-G peptide and/or chimeric modified Con-P peptide, as detailed herein. In some embodiments, the chimeric modified Con-peptide may be administered as a polypeptide as is, or in a suitable pharmaceutical composition. In some embodiments, the chimeric modified Con-peptide may be administered as a polynucleotide molecule encoding for the modified chimeric polypeptide as is, or in a suitable pharmaceutical composition.

According to some embodiments, a therapeutically effective amount refers to an amount sufficient to ameliorate and/or prevent at least one of the symptoms associated with a neurodegenerative condition.

According to some exemplary embodiments, there is provided a method for treating Alzheimer's disease (AD), the method comprising administering to a subject in need thereof a pharmaceutical composition comprising a therapeutically effective amount of a modified Con peptide. In some embodiments, the modified Con peptide is a modified Con-P peptide.

According to some exemplary embodiments, there is provided a method for treating Parkinson's disease (PD), the method comprising administering to a subject in need thereof a pharmaceutical composition comprising a therapeutically effective amount of a modified Con peptide. In some embodiments, the modified Con peptide is a modified Con-P peptide.

According to some exemplary embodiments, there is provided a method for treating ALS, the method comprising administering to a subject in need thereof a pharmaceutical composition comprising a therapeutically effective amount of a modified Con peptide. In some embodiments, the modified Con peptide is a modified Con-P peptide.

According to some exemplary embodiments, there is provided a method for treating Alzheimer's disease (AD), Parkinson's disease (AD), and/or ALS, the method includes administering to a subject in need thereof a pharmaceutical composition comprising a therapeutically effective amount of a modified Con related peptide, wherein the modified Con peptide is a cAPP peptide.

According to some exemplary embodiments, there is provided a method for treating Alzheimer's disease (AD), Parkinson's disease (AD) and/or ALS, the method includes administering to a subject in need thereof a pharmaceutical composition comprising a therapeutically effective amount of a polynucleotide molecule encoding a chimeric modified Con-peptide, said modified Con-peptide is a modified Con-P peptide and/or modified Con-G peptide.

According to some exemplary embodiments, there is provided a method for treating Alzheimer's disease (AD), Parkinson's disease (AD) and/or ALS, the method includes administering to a subject in need thereof a pharmaceutical composition comprising a therapeutically effective amount of a polynucleotide molecule encoding for a chimeric Con-related peptide, such as, cAPP.

According to some embodiments, there are provided kits comprising the modified con-P peptide and/or the nucleic acid molecule encoding the same and/or the composition as disclosed herein. Such a kit can be used, for example, in the treatment of various neurodegenerative conditions.

According to some embodiments, there are provided kits comprising the nucleic acid molecule encoding for the chimeric modified con peptides and/or the compositions as disclosed herein. Such a kit can be used, for example, in the treatment of various neurodegenerative conditions.

According to some embodiments, there are provided kits comprising the modified con-related peptide cAPP and/or the nucleic acid molecule encoding the same and/or the composition as disclosed herein. Such a kit can be used, for example, in the treatment of various neurodegenerative conditions.

Table 1 below lists amino acid sequences a nucleic acid sequences disclosed herein.

TABLE 1

| Name | Sequence (amino acids/nucleotides) | SEQ. ID. NO: |
|---|---|---|
| WT Con-P (*Conus purpurascens*) | GEγγHSKYQγCLRγIRVNKVQQγC | 1 |
| WT Con-G (*Conus geographus*) | GEγγLQγNQγLIRγKSN | 2 |
| WT Con-Pr3 (*Conus parius*) | GEPγVAKWAγGLRγKAASN | 3 |
| Naked Con-P | GEEEHSKYQECLREIRVNKVQQEC | 4 |
| Ala-sub Con-P | GAAAHSKYQACLRAIRVNKVQQAC | 5 |
| Asp-Sub Con-P | GDDDHSKYQDCLRDIRVNKVQQDC | 6 |
| Gly-Sub Con-P | GGGGHSKYQGCLRGIRVNKVQQGC | 7 |
| Naked Con-G | GEEELQENQELIREKSN | 8 |
| Naked Con-G E7A | GEEELQANQELIREKSN | 9 |
| S. (short) Naked Con-G 1-13 | GEEELQENQELIR | 10 |
| S. Naked Con-G E7A 1-13 | GEEELQANQELIR | 11 |
| Alanine-substituted Con-G | GAAALQANQALIRAKSN | 12 |
| Naked Con-Pr3 | GEPEVAKWAEGLREKAASN | 13 |
| Con-G-like APP (cAPP) | ADTDYADGSEDKVVE | 14 |
| Scrambled naked Con-G | NELQQESILERKENEGE | 15 |
| Scrambled naked Con-G | AACGAGCTGCAGCAGGAGAGCATCCTGGAGAGGAAGG AGAACGAGGGCGAG | 16 |
| Naked Con-P | GGCGAAGAAGAGCACAGCAAATACCAGGAGTGCCTGA GGGAGATCAGAGTCAACAAGGTGCAGCAAGAATGT | 17 |
| Ala-sub Con-P | GGCGCCGCCGCCCACAGCAAGTACCAGGCCTGCCTGA GGGCCATCAGGGTGAACAAGGTGCAGCAGGCCTGC | 18 |
| Asp-Sub Con-P | GGCGACGACGACCACAGCAAGTACCAGGACTGCCTGA GGGACATCAGGGTGAACAAGGTGCAGCAGGACTGC | 19 |
| Gly-Sub Con-P | GGCGGCGGCGGCCACAGCAAGTACCAGGGCTGCCTGA GGGGCATCAGGGTGAACAAGGTGCAGCAGGGCTGC | 20 |
| Naked Con-G | GGCGAGGAGGAGCTGCAGGAGAACCAGGAGCTGATCA GGGAGAAGAGCAAC | 21 |
| Naked Con-G E7A | GGCGAGGAGGAGCTGCAGGCCAACCAGGAGCTGATCA GGGAGAAGAGCAAC | 22 |
| S. (short) Naked Con-G 1-13 | GGCGAGGAGGAGCTGCAGGAGAACCAGGAGCTGATCA GG | 23 |
| S. Naked Con-G E7A 1-13 | GGCGAGGAGGAGCTGCAGGCCAACCAGGAGCTGATCA GG | 24 |
| Alanine-substituted Con-G | GGCGCCGCCGCCCTGCAGGCCAACCAGGCCCTGATCA GGGCCAAGAGCAAC | 25 |
| Naked Con-Pr3 | GGCGAGCCCGAGGTGGCCAAGTGGGCCGAGGGCCTGA GGGAGAAGGCCGCCAGCAAC | 26 |

TABLE 1-continued

| Name | Sequence (amino acids/nucleotides) | SEQ. ID. NO: |
|---|---|---|
| Con-G-like APP | GCCGACACCGACTACGCCGACGGCAGCGAGGACAAGG TGGTGGAG | 27 |
| APP-Long scrambled | DEKDSEAVYVDGDTA | 28 |
| Signal Peptide | METDTLLLWVLLLWVPGSTGD | 29 |
| Sig. pep.: | ATGGAGACAGACACACTCCTGCTATGGGTACTGCTGC TCTGGGTTCCAGGTTCCACTGGTGAC | 30 |
| Myc-Tag: | EQKLISEEDL | 31 |
| My c. tag: | GAACAAAAACTCATCTCAGAAGAGGATCTG | 32 |
| Long (L-)linker: | AAAGGGGSGGGGSGGGGSGGGGSGGGGSGGGGSGGGG SGGGGSGGGGSGGGGSGGGGS | 33 |
| Long linker: | GCTGCAGCAGGGGTGGGGGGTCAGGTGGAGGGGGAT CTGGCGGTGGAGGCAGCGGGGGCGGAGGCTCAGGCGG TGGCGGAAGCGGTGGGGGAGGCTCTGGGGGAGGCGGT AGCGGCGGTGGCGGCAGCGGTGGGGGCGGCTCTGGGG GTGGTGGTAGTGGCGGCGGAGGTAGT | 34 |
| Short (S-)linker: | GGGGSGGGGSGGGGSGGGGS | 35 |
| Short linker: | GGTGGTGGCGGAAGTGGGGGCGGTGGAAGTGGTGGAG GTGGGTCCGGTGGAGGTGGGTCC | 36 |
| TMD: | AVGQDTQEVIVVPHSLPFKVVVTSAILALVVLTIISL IILIMLWQKKPR | 37 |
| TMD: | GCTGTGGGCCAGGACACGCAGGAGGTCATCGTGGTGC CACACTCCTTGCCCTTTAAGGTGGTGGTGATCTCAGC CATCCTGGCCCTGGTGGTGCTCACCATCATCTCCCTT ATCATCCTCATCATGCTTTGGCAGAAGAAGCCACGG | 38 |
| ER Export signal Trafficking motif: | TTCTGCTACGAGAACGAGGTG | 39 |
| Golgi-export signal (Swty): | AGAGGCAGATCCTGGACCTAG | 40 |
| EAR16 | GEDDLQDNQDLIRDKSN | 41 |
| EAR18 | GEDDYQDAQDLIRDKSN | 42 |
| APP-Long + 17mer | DDSDVWWGGADTDYADGSEDKVVE | 43 |
| App-short | ADTDYADGSED | 44 |
| ER Export signal | FCYENEV | 45 |
| Golgi-export signal | RGRSWTY | 46 |
| Trafficking motif ERXL | KSRITSEGEYIPLDQIDINVGGSGFCYENEV | 47 |
| Trafficking motif ERXL | AAGAGGAGGATCACCAGCGAGGGCGAGTAGATCCCCC TGGACCAGATCGACATCAACGTGGGCGGCAGCGGCTT CTGCTACGAGAACGAGGTG | 48 |

In the description and claims of the application, the words "include" and "have", and forms thereof, are not limited to members in a list with which the words may be associated. As used herein, the term comprising includes the term consisting of.

As used herein, the term "about" may be used to specify a value of a quantity or parameter to within a continuous range of values in the neighborhood of (and including) a given (stated) value. According to some embodiments, "about" may specify the value of a parameter to be between 80% and 120% of the given value. According to some embodiments, "about" may specify the value of a parameter to be between 90% and 110% of the given value. According to some embodiments, "about" may specify the value of a parameter to be between 95% and 105% of the given value.

As used herein, according to some embodiments, the terms "substantially" and "about" may be interchangeable.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Molecular Biology: Synthesized and purified peptides were provided by Alomone Labs, Israel), according to the requested peptide sequences. Lyophilized peptide powders were kept in room temperature and dissolved prior to experiments in recording solutions and were either immediately used or kept in 4° C. for several days. All small molecule toxins and receptor modulators (provided by Alomone Labs, Israel), were dissolved in H$_2$O and kept in –20° C.

mRNA for expression of neuroreceptors in oocytes was produced from cDNA clones. cDNA was enzymatically linearized and then mRNA was yielded using mMES SAGE mMACHINE transcription kit (Invitrogen™) and stored in –80° C. until use.

*Xenopus* oocytes extraction and maintenance: Adult *Xenopus* frogs were anesthetized and a minor abdomen cut was made to extract a portion of the ovary. Oocytes were folliculated by treatment with collagenase and then kept in NDE-96 solution (ND-96 solution added with Penicillin-Streptomycin and sodium-pyruvate). One day after surgery, oocytes were injected with 50 nl mRNA each, and incubated in 18° C. for 1-3 days before recordings.

Mammalian cell cultures maintenance and transfection: HEK293T cells were grown on 90-mm plates in Dulbecco's Modified Eagle Medium (DMEM, Biological Industries™) in 37° C. Prior to transfection, cells were moved to 35-mm plates for overnight incubation and then transfected for NMDAR expression using ViaFect transfection reagent (Promega™) and 1-2 μg cDNA per plate. 6 hours after transfection, cells were moved to 24-well plates containing PDL-covered glass coverslips and were added with 200 μM AP-5 and 2 μM MK-801 toxins for prevention of NMDAR-induced toxicity. cells were then incubated for 1-2 days prior to recordings.

Hippocampal neurons were extracted from hippocampi of day 0 neonate rats and transferred to 24-well plates containing PDL-covered glass coverslips and MEM (Gibco™)-based neuronal growth medium. 7-9 days old neurons were infected with AAV-syn-jGCaMP7f virus and incubated for 3-4 more days prior to recordings.

Electrophysiological recordings: Oocytes were recorded using a two-electrode oocyte clamp OC-725C amplifier (Warner Instruments) and Digidata 1550B digitizer (Axon Instruments). For dose-response and competitiveness experiments, oocytes were gravity-perfused with different toxin (modified con-peptides or native con peptides) concentrations dissolved in BARTH solution (in mM): 100 NaCl, 0.3 BaCl2, 5 HEPES, pH=7.3-7.4 and voltage-clamped at –60 mV. Importantly, as calcium disrupts recordings in oocytes due to activation of calcium dependent chloride channels, the recording solution was nominally calcium and magnesium free (to avoid block of receptors). The experiment was also repeated with calcium-containing ND-96 solution (in mM): 96 NaCl, 2 KCl, 1 CaCl2, 1 MgCl2, 5 HEPES, pH=7.3-7.4, where only brief pulses of agonists were given so that receptor activation yielded brief responses, thus avoiding non-NMDAR artifacts. For voltage-dependence experiments, oocytes were recorded using a custom protocol where a holding of –60 mV was briefly changed to a 1-sec voltage gradient of –120 to +120 mV, in two times divided by 30 secs during which toxins were perfused. For calcium-containing experiments of toxin dose-responses, oocytes were perfused for >30 secs before being exposed to a brief 3 secs pulse of agonists.

HEK293T cells were whole-cell voltage clamped at –70 mV using a Multiclamp 700B amplifier and Digidata 1440A digitizer patch system (Axon Instruments) with 3-7 MOhm glass pipettes filled with intracellular solution (in mM: 135 K-gluconate, 10 NaCl, 10 HEPES, 2 MgCl2, 2 Mg-ATP, 1 EGTA, pH=7.3). Cells were gravity perfused with increased concentrations of peptides, similar to the oocyte's experiments. Cells were recorded in NMDAR recording solution (in mM: 138 NaCl, 1.5 KCl, 2.5 CaCl$_2$), 10 D-glucose, 5 HEPES, 0.05 glycine, pH=7.4).

Calcium-imaging of cultured hippocampal neurons: coverslips with infected neurons were positioned under a Zeiss laser scanning confocal microscope (LSM-880, Zeiss group) in NMDAR recording solution. Excitation of jGCaMP7f was obtained with a 488 nm laser. Cell fluorescence was continuously recorded for a baseline period of several minutes, followed by gravity perfusion of increasing peptide concentrations, each for several minutes. recordings ended with a wash period of several minutes. Recordings were taken from a few fields from each coverslip to confirm that the peptides are reversible and do not induce cell deterioration.

Data analysis and statistics: Data from Axon pCLAMP-10™ electrophysiological recordings was extracted to Excel files, where each toxin-concentration data point was subtracted of leak current and normalized to the baseline response current. Values of each concentration from all cells of each experimental group were averaged and SEM was calculated. SigmaPlot (Systat) software was used to calculate IC50 values for all dose-response experiments based on the Hill fit curve ($f=1-x^b/(c^b+x^b)$) and to test for statistical significance of differences among groups (student's t-test or ANOVA under alpha of 0.05, unless stated otherwise).

Imaging data was extracted using ZEN software (Zeiss group). Dendrites were manually and randomly chosen and fluorescent data points were collected from each of them and extracted to Excel files. Each recorded trace vector was then corrected for artifacts and normalized to basal fluorescence to yield delta F/F values. A custom MATLAB (MathWorks) script was used to detect calcium transients and calculate their numbers, averages and SEMs, and frequencies for each peptide concentration epoch for each experimental group. SigmaPlot software was used to test for statistical significance of differences among groups (ANOVA under alpha of 0.05).

Example 1: Stability of Modified Con-G and Con-P Peptide

Figure 3B:
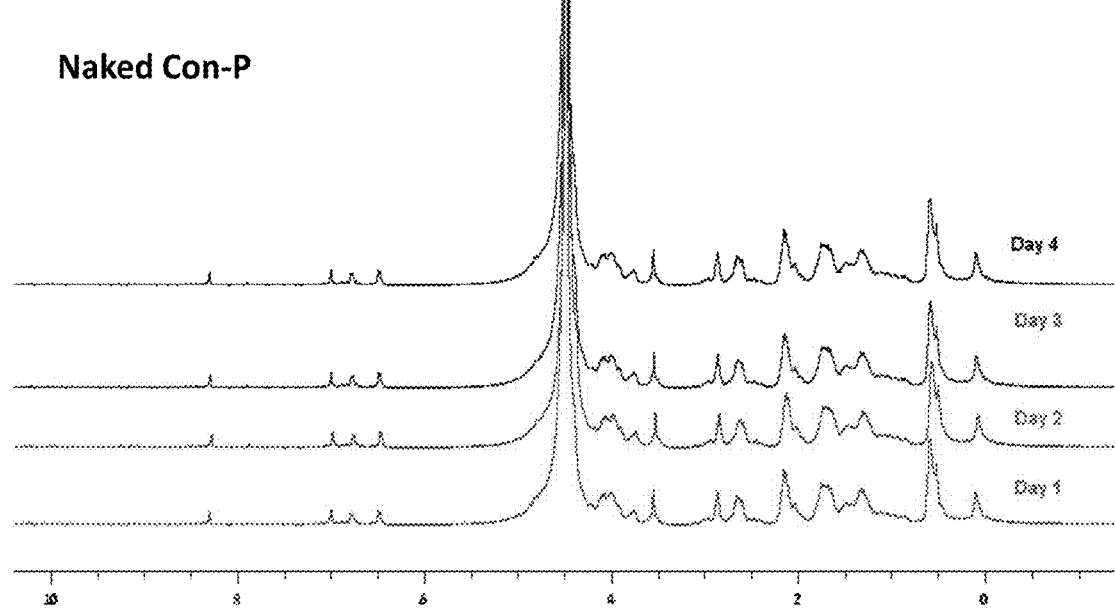

The stability of naked Con-G and naked Con-P at room temperature was determined using NMR analyses, over a period of four days. The results are presented in FIGS. 3A-B. As can be seen in FIGS. 3A-B, the soluble modified peptides are stable in room temperature over an extended period of time. The results suggest that such modified peptides maintain their structure and are comparable in stability to a corresponding native Con-peptide.

Example 2: Modified Con-G Peptide is a NMDAR Inhibitor

NMDA receptor subunits were expressed in *Xenopus* oocytes, as detailed above. Response of the expressed receptors, as recorded by two-electrode voltage clamp was performed in the presence of native Con-G peptide, or naked con-G peptide.

The results are presented in FIGS. 4A-F. As can be seen in FIGS. 4A and 4B—traces of GluN2A/B subtypes responses to increasing concentrations of Native Con-G in *Xenopus* oocytes, as recorded by two-electrode voltage clamp. FIG. 4C shows a Dose-response curves of the Native Con-G. As can be seen in FIGS. 4D and 4E—traces of GluN2A/B subtypes responses to increasing concentrations of modified Con-G (naked Con-G) in *Xenopus* oocytes, as recorded by two-electrode voltage clamp. FIG. 4F shows a Dose-response curves of the naked Con-G.

The results demonstrate that the modified Con-G peptide is indeed an NMDAR inhibitor, similarly to a native Con-G peptide.

Example 3: Modified Con-G Peptide is Non-Competitive and Voltage-Dependent

NMDA receptor subunits were expressed in *Xenopus* oocytes, as detailed above. Response of the expressed receptors, as recorded by two-electrode voltage clamp was performed in the presence of native Con-G peptide, or naked con-G peptide and in the presence of low and saturating concentration of glutamate.

The results are presented in FIGS. 5A-G. Shown in FIGS. 5A and 5B are traces of GluN2B subtype responses to Native or Naked Con-G in a low and saturating concentration of glutamate, in *Xenopus* oocytes, as recorded by two-electrode voltage clamp. FIG. 5C shows Comparison between Native and Naked Con-G competitiveness. FIGS. 5D and 5E show traces of voltage-gradient responses of GluN2B expressed in oocytes, pre and post treatment with either Native or Naked Con-G. FIGS. 5F and 5G show Current-Voltage curves summary. Black and color (originally) horizontal bars represent agonists and toxin application, respectively. ***P<0.001.

The results demonstrate that the modified Con-G peptide is non-competitive and is voltage-dependent.

Example 4: NMDAR Receptors are Specifically Inhibited by a Wide Range of Modified Con-G Peptides when Expressed in *Xenopus* Oocytes NMDA receptor subunits were expressed in *Xenopus* oocytes, as detailed above. Response of the expressed receptors, as recorded by two-electrode voltage clamp was performed in the presence of various modified Con-peptides. The results are presented in FIGS. 6A-F. Shown in FIG. 6A are GluN2A/B subtypes responses to a variety of modified Con-G peptides (sequences of which are detailed in Table 1, above herein). Shown in FIGS. 6B and 6C are trace and summary of GluN2B subtype response to a high concentration of scrambled Naked Con-G control peptide (SEQ ID NO: 15). Shown in FIG. 6D and FIG. 6E Trace and summary of GluN2B subtype response to increasing concentrations of alanine-substituted Con-G peptide (SEQ ID NO: 12). Shown in FIGS. 6F and 6G are trace and summary of GluA1/2 AMPAR response to Naked Con-G. Cyclothiazide (CTZ) was used for preventing AMPAR desensitization. Black and grey horizontal bars represent agonists and toxin application, respectively.

The results demonstrate that NMDAR, but not AMPAR, is inhibited by a wide range of modified Con-G peptides in high concentrations in *Xenopus* oocytes.

Example 5: Naked Con-G Reduces NMDAR-Dependent Excitatory Postsynaptic Currents (EPSCs)

Figure 7A:
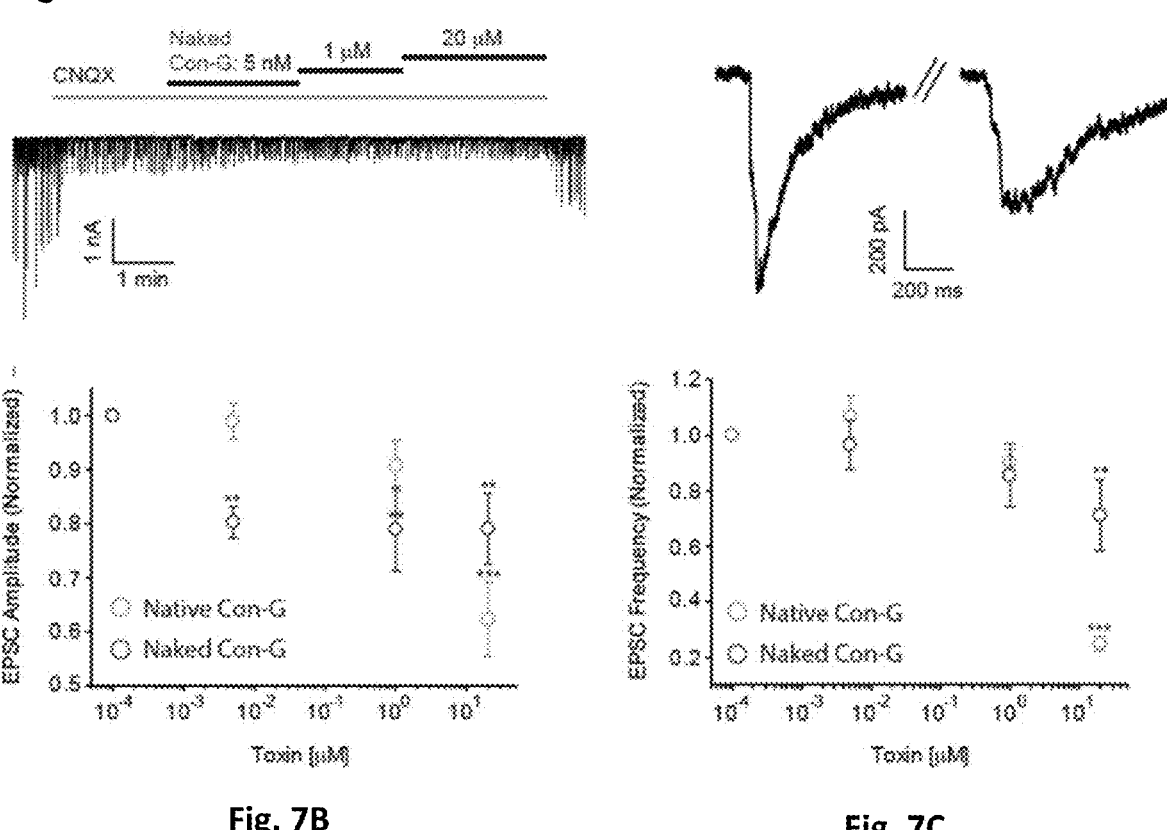
FIG. 7A shows representative recording of NMDARs-dependent EPSCs, inset average EPSC before and after 5 nM of incubation with modified Con-G peptide.

FIG. 7A shows Representative recording of NMDARs-dependent EPSCs, inset average EPSC before and after 5 nM of incubation with modified Con-G peptide. FIG. 7B shows a Summary of spontaneous EPSCs amplitude and FIG. 7C shows Summary of spontaneous EPSCs frequency, in the presence of modified Con-G or native Con-G peptide. grey bar-CNQX 10 μM, entire experiment with Bicuculline 10 μM, QX-314.

The results demonstrate that indeed, the modified Con-G peptide can inhibit NMDAR-dependent Excitatory postsynaptic currents (EPSCs) in target cells.

Example 6: Naked Con-G Inhibits NMDAR in HEK293 Cells

Figure 8:
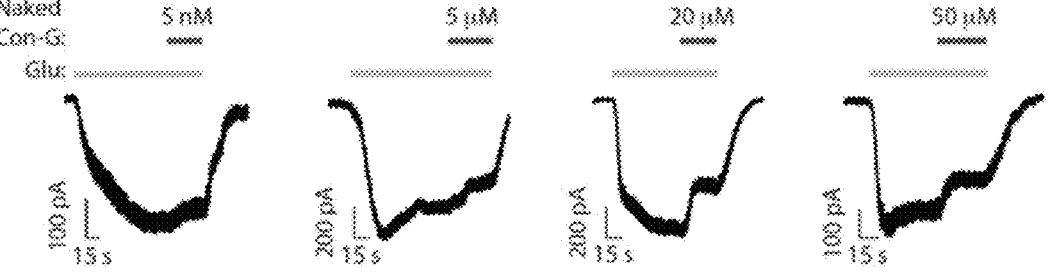
FIG. 8 graphs showing effect increasing amounts of modified Con-G peptide (naked Con-G), in the presence of Glutamate and 2.5 mM Ca' on GluN2B-NMDARs receptors were expressed in HEK293 mammalian cells.

NMDARs were expressed in HEK293 mammalian cells. The cells were incubated with increasing amounts of modified Con-G peptide (naked Con-G), in the presence of Glutamate and 2.5 mM $Ca^2$. The results are presented in FIG. 8, which demonstrate that in HEK293t cells, the modified Con-G peptide behaved similarly as in *Xenopus* oocytes, reaching ~30% inhibition at 50 μM (32.3±5.96% inhibition, n=5). Thus, naked con-G inhibits NMDARs in HEK293 cells.

Taken together, the results presented in Examples 1-6 above demonstrate that the modified con-G peptides are functional. It may appear that unlike the native con-G, they exhibit somewhat lower potency, are non-competitive, weak voltage-dependent, display biphasic inhibition, and remain NMDARs-specific, as they do not inhibit AMPARs (100 μM naked con-G on ImaxAMPA=0.96±0.017%, n=14). Alanine-substituted or scrambled naked con-G peptides did not have any effect on 2A or 2B-receptors; when used up to 50 μM. In HEK293t cells, naked con-G behaved similarly to its activity in *Xenopus* oocytes, reaching ~30% inhibition at 50 μM (32.3±5.96% inhibition, n=5). In neurons, naked con-G significantly reduced synaptic NMDAR-dependent spontaneous EPSCs's amplitude, even more so than the native con-G peptide at low concentrations and both native and naked toxins had less effect on frequency. The same was observed when measuring NMDA-dependent miniature EPSCs (minis), namely amplitude tended to reduce (~15%) without any effect on frequency.

Thus, collectively, the results show that modified con-G peptides are functional in mammalian cells, importantly neurons.

Example 7: Naked Con-Pr3 Inhibits NMDAR in HEK293 Cells

Figure 9:
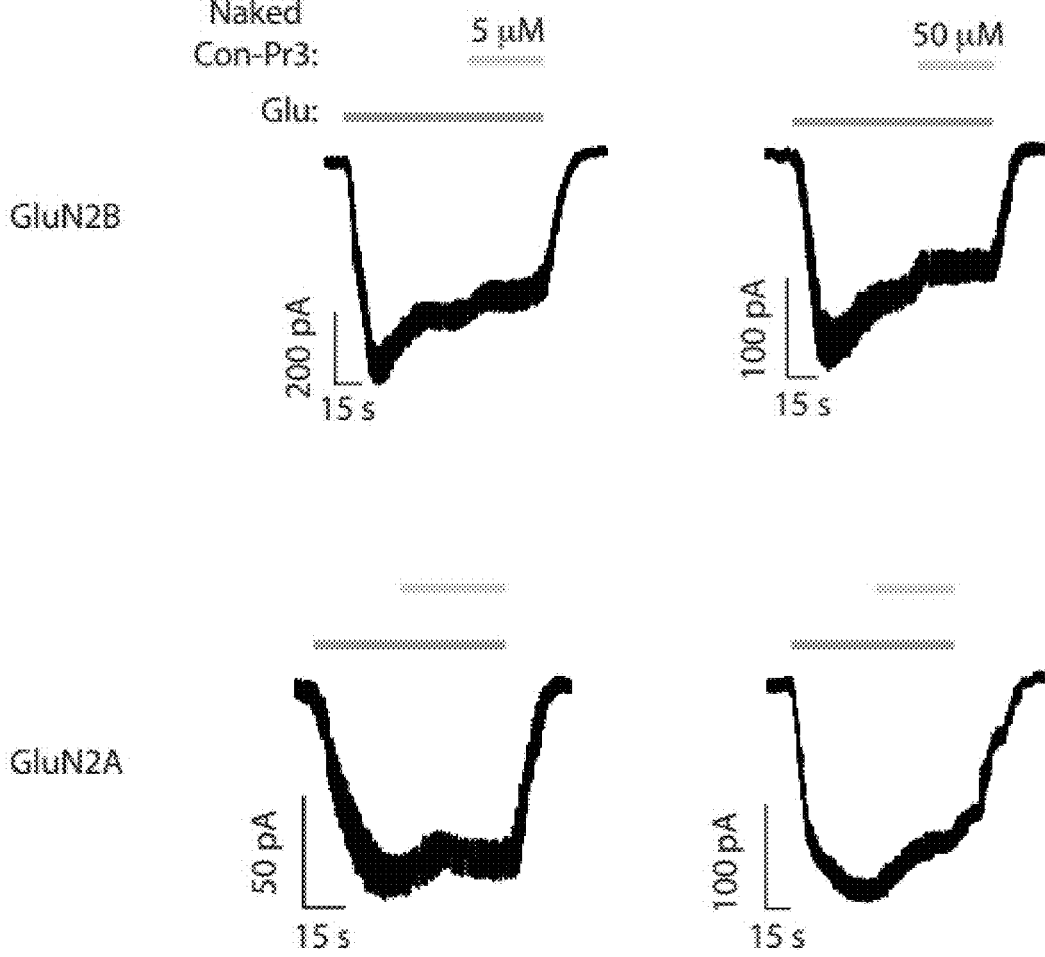
FIG. 9 shows graphs of traces of GluN2B, 2A subtypes responses to Naked Con-Pr3 in HEK293T cells as recorded by whole-cell voltage clamp.

Traces of GluN2B, 2A subtypes responses to Naked Con-Pr3 in HEK293T cells were recorded by whole-cell voltage clamp. The results are shown in FIG. 9, demonstrating the inhibitory effect of the naked Con-Pr3 on the NMDARs. The results indicate the naked Con-Pr3 behaves similarly to naked Con-G peptides.

Example 8: Modified Con-P Exhibit Differential Effect on NMDAR Subtypes

Traces of GluN2B, 2A subtypes responses to modified Con-P (naked, Asp-Sub) in HEK293T cells were recorded by whole-cell voltage clamp.

The results presented in FIG. 10A, show the inhibitory effect of modified Con-P on GluN2B (NR2B) containing NMDARs. The results presented in FIG. 10B, show that modified Con-P potentiates GluN2A (NR2A) containing NMDARs. FIG. 10C presents dose response curves of the effect of Con-P on activity of NR2B and NR2A containing NMDARs.

Figures 11A, 11B, 11C, 11D:
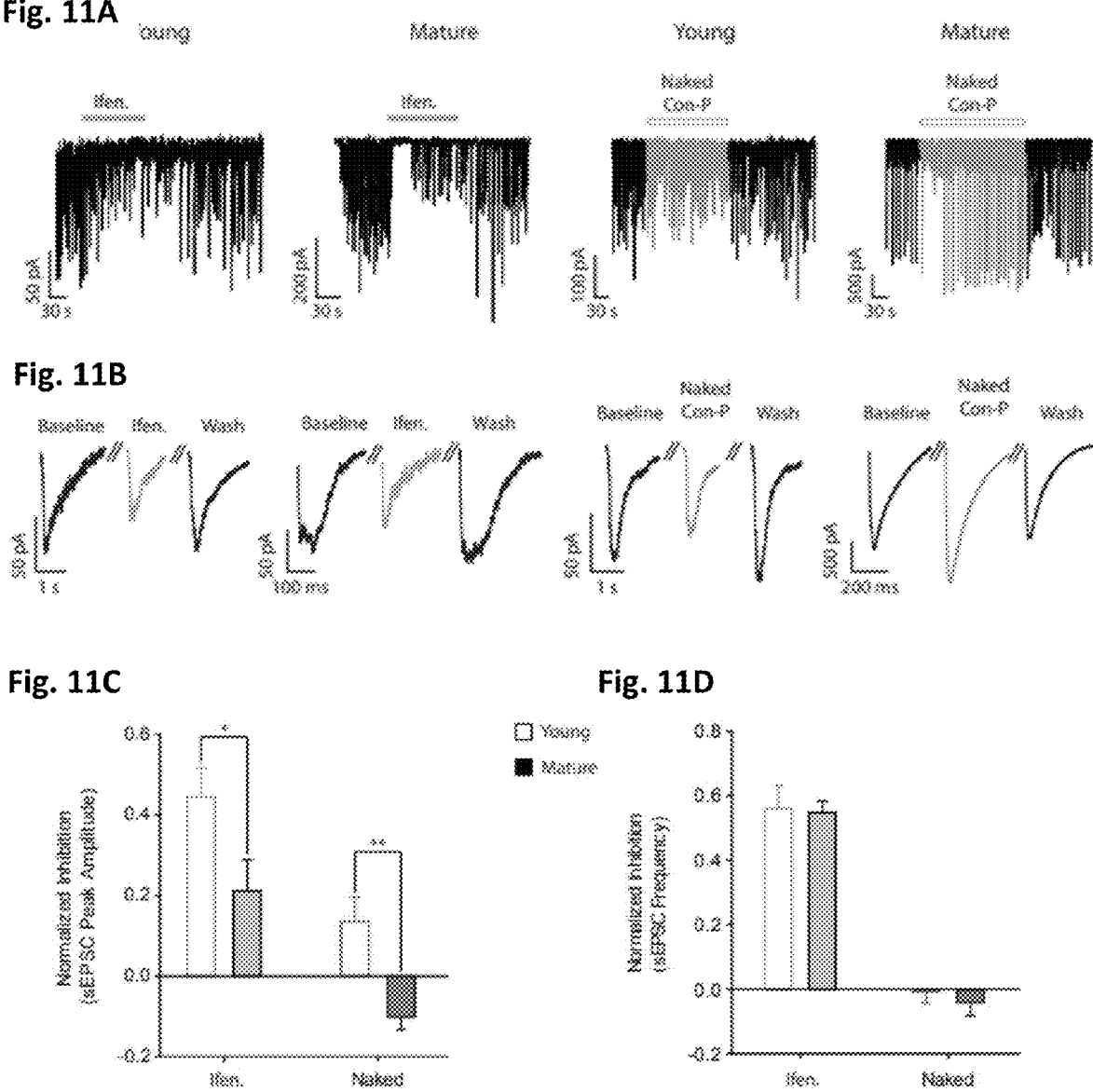
FIGS. 11A-D show ESPCs of young and mature cultured Hippocampal neuron cells treated as with ifenprodil and modified con-P.

Example 9: Differential Effect of Ifenprodil and Modified Con-P on NMDAR-Dependent Excitatory Postsynaptic Currents (EPSCs) of Young and Mature Cultured Hippocampal Neurons Hippocampal neurons were obtained as detailed above. The cells were treated as detailed above with ifenprodil and modified con-P (naked con-p, Asp-Sub con-P). ESPCs of young and mature cultured cells were detected. The results are presented in FIGS. 11A-D. The results clearly show that Naked con-P enhances GluN2A (NR2A)-dependent EPSCs. FIG. 11A—shows representative recording of NMDAR-dependent EPSCs, before and after application of naked con-P, in young or mature neurons. FIG. 11B shows averaged EPSCS before, during and after treatment (ifenprodil—grey; naked con-P- (originally) cyan). Entire expt. CNQX 10 μM, Bicuculline 10 μM, QX-314 (intra solution), summarized in FIGS. 11C-D.

Collectively, the results presented in Examples 8-9 demonstrate that modified con-P exhibits a unique and undescribed behavior: it inhibits GluN2B and further, surprisingly, it produced robust potentiation of GluN2A-currents in HEK293t cells. Importantly, this was also apparent in primary neurons (isolated NMDAR-dependent spontaneous EPSCs; FIGS. 11A-D). Application of modified con-P onto young neurons (4 DIV-synapses mostly containing GluN2B-subunits) showed inhibition of NMDARs-dependent EPSCs, akin to ifenprodil (GluN2B-specific antagonist) (FIGS. 11A-B, Young). However, application of naked con-P onto mature neurons (13 DIV-synapses mostly containing GluN2A) (FIGS. 11A-B; Mature) showed the exact inverse from ifenprodil, namely potentiated synaptic currents. Thus, modified con-P potentiates endogenous synaptic GluN2A-receptors in neurons (FIGS. 11C-11D).

Thus, the results indicate that naked con-P exhibits remarkable properties—not only can it inhibit (but not eliminate) extrasynaptic-2B currents, it also enhances GluN2A-receptors at the synapse, thereby capable of promoting plasticity and cognitive enhancement.

Example 10: APP Related Peptide Inhibit NMDARs

NMDA receptor subunits were expressed in *Xenopus* oocytes, as detailed above. Response of the expressed receptors, as recorded by two-electrode voltage clamp was performed in the presence of cAPP peptide.

Figure 12A:
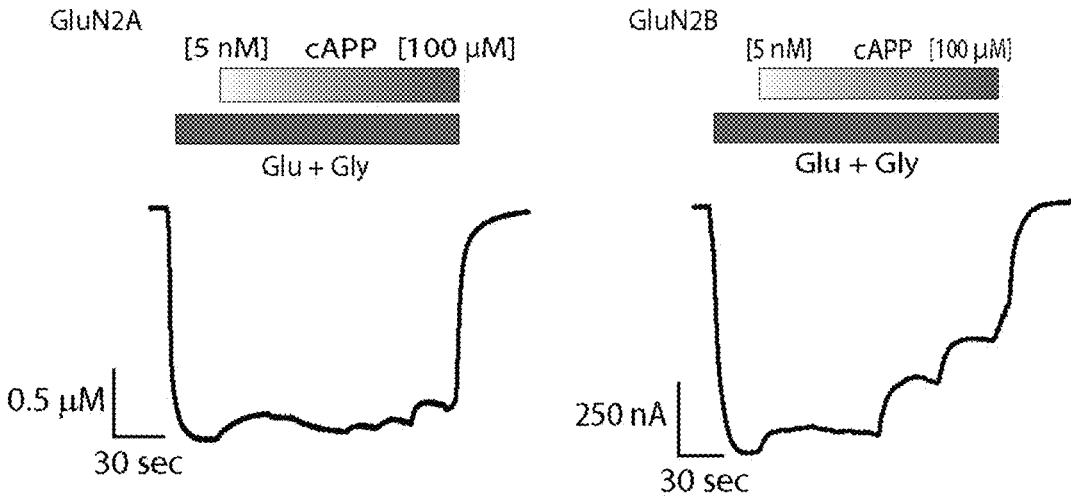
FIGS. 12A-12B shows representative GluN2A and Glu-2B currents in *Xenopus* oocytes, in the presence of increasing amounts of cAPP (FIG. 12A); The graphs shown in FIG. 12B summarize the results of the effect of increasing amounts of cAPP on activity of GluN2A and Glu-2B.
Figure 12B:
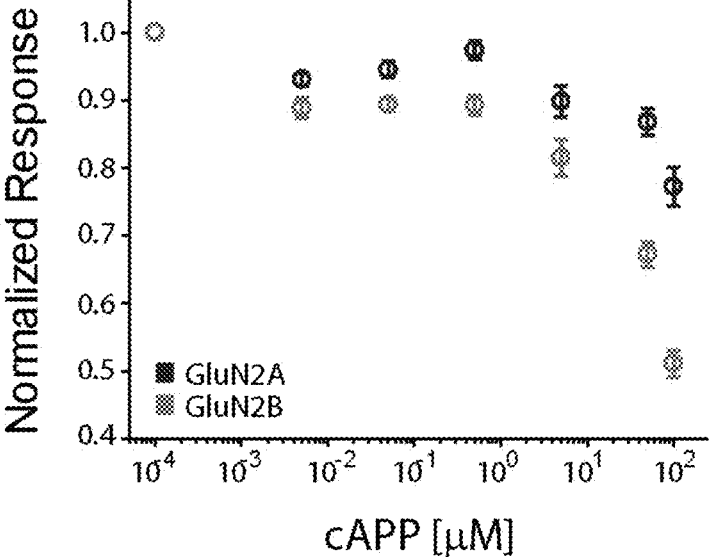

The results are presented in FIGS. 12A-B. FIG. 12A shows representative GluN2A and Glu-2B currents in the *Xenopus* oocytes, in the presence of increasing amounts of cAPP, and FIG. 12B shows summary of the results.

Taken together, the results demonstrate inhibition of NMDARs by incrementing cAPP concentrations.

Example 11: APP Related Peptide and is a Full Agonist of GABABbRs and Modified Con-G Peptide Activates GABAbRs GABAbRs were expressed in *Xenopus* oocytes. Potassium currents (GIRK channel) induced by activation of GABAb1a/2 receptor in *Xenopus* oocytes were determined in the presence of various modified Con-G peptides or APP related peptides.

Figures 13A, 13B, 13C, 13D, 13E, 13F:
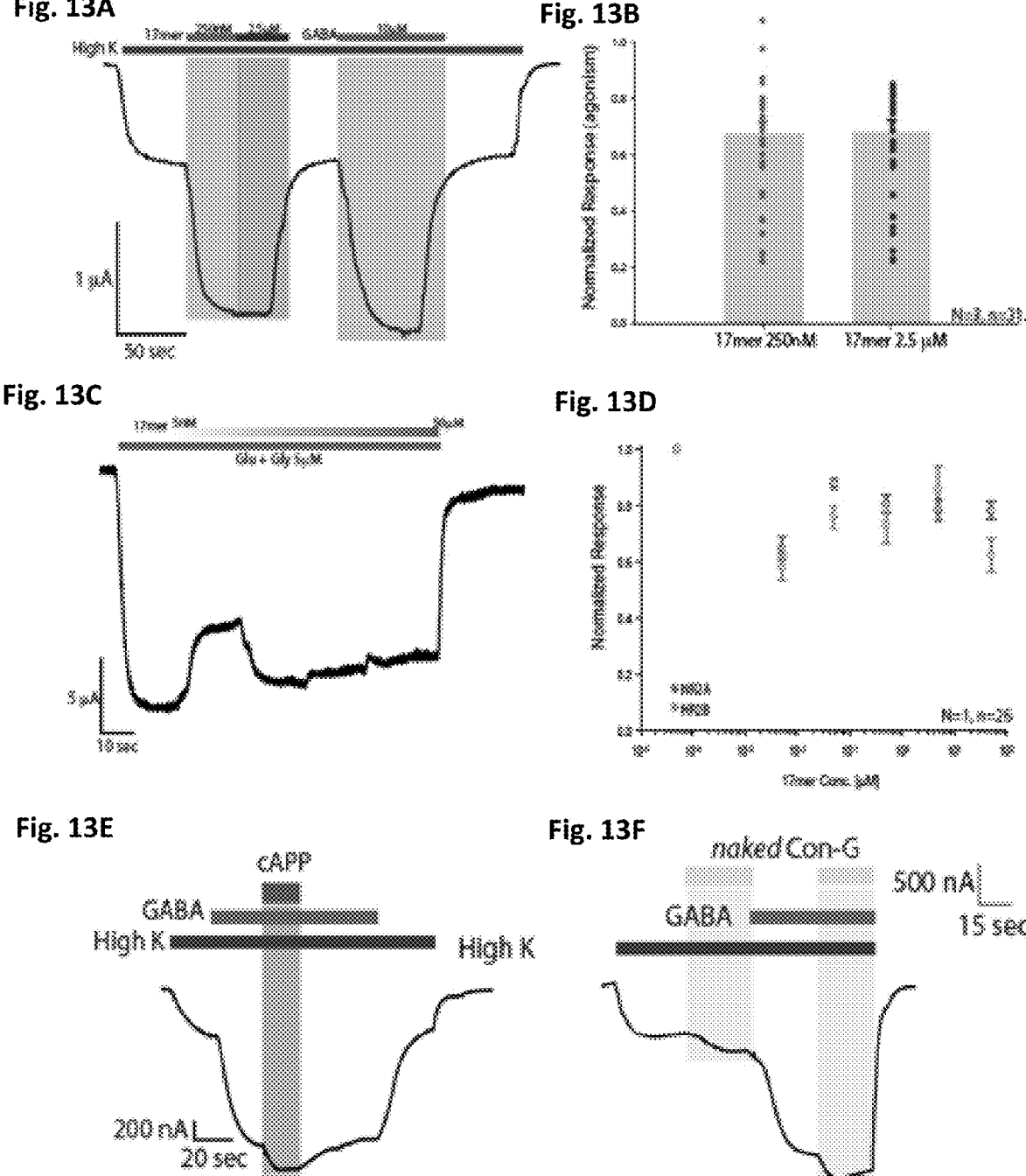
FIGS. 13A-13B show representative potassium currents (GIRK channel) induced by activation of GABAb1a/2 receptor in *Xenopus* oocytes by application of 250 nM or 2.5 uM of the 17-mer APP peptide (SEQ ID NO: 17) or GABA.
FIGS. 13C-13D show the inhibitory effect of the 17-mer on NMDARs-currents.
FIG. 13E show the effect of cAPP on GABAbRs activation.
FIG. 13F show the effect of naked con-G on activation of GABAbRs.

The results are presented in FIGS. 13A-F. Shown in FIG. 13A are Representative potassium currents (GIRK channel) induced by activation of GABAb1a/2 receptor in *Xenopus* oocytes. Application of high potassium media reveals the basal activity of GIRK. Then, activation of the receptor directly by 250 nM or 2.5 μM of the 17-mer APP peptide (SEQ ID NO: 17) fully opens the channel to similar extent as application of GABA (the ligand of GABAbRs), as shown in FIG. 13B. FIGS. 13C-D show the inhibitory effect of the 17-mer inhibits NMDARs-currents. FIG. 13E show the effect of cAPP on GABAbRs activation and FIG. 13F show the effect of naked con-G on activation of GABAbRs.

Collectively, the results presented in Examples 10-11 demonstrate that in oocytes, cAPP preferentially inhibited 2B-currents (up to 30%) over 2A currents (FIG. 11). Inhibition was not competitive and weakly voltage-dependent, both of which were also observed when using naked con-G. Thus, we find functional similarity (in addition to sequence) between these peptides.

Further, when 17-mer APP, cAPP or naked Con-G were tested for their effect onto GABAb 1a/2-activated K+-currents surprisingly it was found that 17-mer APP is a full-agonist (directly activates GABAb1a/2R) (FIG. 13A-B). GABAbR currents were increased both with and without application of the ligand GABA. 17-mer APP also inhibited NMDARs currents, albeit to a lesser degree than cAPP or naked con-G (FIGS. 13C-D). cAPP and naked con-G also showed positive activity towards GABAbRs (opening the receptor; FIGS. 12E-F, respectively).

Taken together, it was found that the mechanism of 17-mer towards GABAbRs involves acting as a full agonist, suggesting that its very strong inhibitory effect on neuronal activity also incorporates inhibition of postsynaptic NMDARs. Naked con-G and cAPP act in a similar manner, both inhibiting NMDAR and activate/potentiate GABAbRs to collectively inhibit ex-GluN2B-receptor, reduce Ca2+- overload and promote suppression of neuronal hyperexcitability; ultimately leading to rescue of neurons in the diseased brain.

Example 12: Membrane Associated Modified Con-G Inhibits NMDARs at Membrane

Chimeric modified Con-G polypeptides were prepared as detailed herein and expressed in mammalian HEK293 cells. Their expression in the cells was determined and their effect on NMDARS activity was determined.

FIG. 14A shows a Cartoon representation of the membrane-associated modified Con-G chimeric polypeptide, illustrating the membrane-associated modified Con-G moiety, and the membranal NMDAR subunits. FIG. 14B shows Micrograph images showing the membranal expression of the modified con-G polypeptide, as determined by fluorescence imaging of the fluorescent marker (dsRed). FIG. 14C shows Glutamate dose-response curves for GluN1a/GluN2B receptors expressed in HEK293 cells, with (right) or without (left) the membranal modified-Con-G polypeptide. The results are summarized in the graphs shown in FIG. 14D. FIG. 14E shows Maximal current compared between groups with (white bars) or without (black bars) co-expression of the membranal modified-Con-G polypeptide (pA/pF) (n=10).

Next, the membranal polypeptides are tested for their ability to protect against excitotoxicity-induced cell death. To this aim, apoptosis is induced (by excessive glutamate application) in cultured hippocampal neurons and cell viability (and death) is determined over time using fluorescent dyes high throughput imaging (Incucyte).

Thus, expression in HEK293t cells showed that the chimeric modified Con-G properly traffics to plasma membrane (FIG. 14B). Functionally, it slightly affected glutamate's potency (FIGS. 14C-D), but, importantly, reduced the maximal current obtained by 100 µM glutamate (FIG. 14E). These go together to show that the chimeric modified Con-G behaves as a non-competitive weak antagonist.

Collectively, the results demonstrate the membranal expression of the modified Con-G peptide and that the expressed modified polypeptide is active and capable of reducing currents of Glu1A/GluN2B in mammalian cells (HERK293t) without affecting affinity for Glutamate (the ligand).

Example 13: Membrane Associated Modified Con-P is Expressed at the Cellular Membrane Chimeric modified Con-P polypeptides (including naked Con-P or Asp-sub. Con-P or Ala-Sub Con-P and) were prepared as detailed herein and expressed in mammalian HEK293 cells without or together with GluN2B subunit. Their expression in the cells was determined and their effect on NMDARS activity was determined.

The results are presented in FIGS. 15A-B. As shown in the pictograms presented in FIG. 15A the expression of the modified Con-P is indeed confined to the membranes (as determined by detection of the C-Myc tag (Green), ds-Red fluorescent signal (red emitted from the fluorescent protein marker) and DAPI staining of the cells' nucleus. Further, as shown in the pictograms presented in FIG. 15B, the expression of the receptor in the cells does not affect the expression of the modified polypeptide, and vice-verse. Furthermore, the receptor and the modified polypeptide co-express and co-localize in the cells. The results are quantitated in the graphs on the right hand panel of FIG. 15B. The membranal polypeptides are further tested for their effect on the expressed NMDAR as well as their ability in protecting against excitotoxicity-induced cell death. To this aim, apoptosis is induced (by excessive glutamate application) in cultured hippocampal neurons and cell viability (and death) is determined over time using fluorescent dyes high throughput imaging (Incucyte).

Example 14: Expressing Chimeric Modified Con-Peptides In-Vivo for Suppression of Excitotoxicity and Alleviation of Cognitive Deficits in Animal Models of Neurodegeneration Next, the chimeric modified Con-peptides (including Con-G, Con-P, Con-Pr3. cAPP) are expressed in brains of behaving animals. To this aim, the nucleic acid molecule expression cassettes are incorporated into AAVs (adeno associated virus) for neuronal infection by stereotactic injections to selected brain regions of mice. An AD mouse model is used, thereafter, mainly the hippocampal formation with be targeted for expression of the chimeric polypeptides. The expression and functionality are assessed (expression, cellular localization, examine neurodegeneration), as described above, for example, using acute hippocampal slices. This is followed by assessing the behavior of AD mice, with or without the expression of the chimeric polypeptides, using a battery of highly-validated hippocampus-dependent memory behavioral tests.

Briefly, whole brains are removed, stained for neuronal and synaptic markers, cleared (CLARITY/uDISCO97); then imaged by light-sheet microscopy. This allows examining the extent of degeneration (and survival) of neurons across the entire brain. These features are compared between hemispheres and control (non-treated) animals. Neuronal function (and extent of neuronal death/survivability) is performed in acute slices from AD mice by electrophysiology. Hippocampus-injected animals are behaviorally-assessed for spatial learning, commonly by protocols including the active place avoidance tasks, navigation or Morris water maze; which are well-suited for hippocampal dysfunction in AD-mice. Performance between injected and non-injected animals is compared. Additionally, large-scale neural activity (systems level) is compared in treated WT-mice (treated meaning the mice are administered (by injection) with the chimeric modified Con-peptides expressing vectors). In WT mice, mimicry of AD is achieved by Aβ-dependent neuronal hyperactivation by application of a synthetic Aβ in vivo. To this aim, the animals are co-administered (co-injected) with GCaMP7s or iGluSnFR (a fluorescent glutamate sensor that has been modified to localize to extrasynapse) together with the chimeric modified Con-peptides expressing vectors. Animals are imaged by 2-photon microscopy or miniature head-mounted endoscope (miniscope). The miniscope allows to examine neural activity in freely behaving animals and therefore allows testing whether neuronal activity (via imaging of GCaMP) is changed during neuronal navigation, with or without the chimeric modified-Con polypeptides.

What we claim is:

1. A modified conantokin-P (con-P) peptide comprising at least one amino acid residue substitution as compared to a naturally occurring native conantokin-P peptide, wherein the amino acid substitution comprises substitution of at least one gamma carboxyglutamate acid residue of the naturally occurring conantokin-P with at least one amino acid selected from the group consisting Aspartate, Alanine and Glycine, wherein the modified con-P peptide comprises the amino acid sequence as denoted by any one of SEQ ID NOs: 5-7.

2. The modified con-P peptide according to claim 1, wherein the modified con-P peptide is capable of modulating activity of GluN2B NMDA receptor subunit and/or GluN2A NMDA receptor subunit in cells, wherein the modulation comprises reducing activity of GluN2B receptor subunit and/or increasing activity of GluN2A receptor subunit.

3. The modified con-P peptide according to claim 1, wherein the modified con-P peptide is capable of inhibiting activity of GluN2B receptor subunit when expressed in extrasynaptic region of neuronal cells and/or wherein the modified con-P peptide is capable of enhancing activity of GluN2A receptor subunit in the synaptic region of neuronal cells.

4. The modified con-P peptide of claim 1, wherein the modified con-P peptide is encoded by a vector comprising a nucleic acid molecule encoding for the modified con-P peptide, said nucleic acid molecule comprises a nucleotide sequence as denoted by any one of SEQ ID NOs: 18-20.

5. The modified con-P peptide according to claim 4, wherein the vector is an expression vector, further comprising one or more additional nucleic acid sequences selected from: regulatory sequences, localization sequence, a tag sequence, a marker sequence, or combinations thereof.

6. A host cell comprising the modified con-P peptide of claim 4, wherein the host cell is transformed or transfected with the vector.

7. A vertebrate host cell comprising the modified con-P peptide according to claim 1.

8. A nucleic acid molecule for expressing a chimeric modified conantokin polypeptide in or on a membrane of a target cell, the nucleic acid molecule comprising:
   a first nucleotide sequence encoding for a modified conantokin peptide, wherein the modified conantokin peptide is a modified conan tokin-P (con-P) peptide comprising the amino acid sequence as denoted by any one of SEQ ID NOs: 5-7;

a second nucleotide sequence encoding for a transmembrane domain, capable of directing the expressed modified conantokin peptide to the membrane; and
   a third nucleotide sequence, being a regulatory sequence capable of affecting expression of the modified conantokin peptide within the target cell.

9. The nucleic acid molecule according to claim 8, further comprising one or more nucleic acid sequences encoding for: a signal peptide, a marker sequence, a linker sequence and/or a tag sequence.

10. The nucleic acid molecule according to claim 8, wherein the first nucleotide sequence encoding for the modified conantokin peptide comprises a nucleotide sequence as denoted by any one of SEQ ID NOs: 18-20.

11. The nucleic acid molecule according to claim 8, wherein the transmembrane domain (TMD) encoded by the second nucleotide sequence is a TMD derived from the PDGF receptor; and/or wherein the third nucleotide sequence comprises a CMV promoter sequence, a CAG promoter sequence, a promoter sequence derived from a promoter sequence of a gene for a LINGO protein or a human synapsin (hSyn) protein, or a promoter sequence derived from a promoter sequence of a gene selected from the group consisting of: RASGEF1B, SLC26A3, GNAI2, NEK6, UBE2D3, CDC42EP4, ERCC3, BBC3, FOXO1, CASP3, CLCA1, and GFAP.

12. The nucleic acid molecule according to claim 8, being an expression cassette of a viral expression vector.

13. The nucleic acid molecule according to claim 8, wherein the modified conantokin peptide encoded by the first nucleotide sequence is capable of modulating activity of one or more subunits of NMDA receptor.

14. A host cell comprising the nucleic acid molecule according to claim 8.

15. A chimeric polypeptide comprising a modified conantokin peptide domain and a transmembrane domain operably linked to the modified conantokin peptide domain, wherein the transmembrane domain is capable of directing the chimeric polypeptide to a cellular membrane in a target cell, wherein the modified conantokin peptide domain is a modified conantokin-P (con-P) peptide domain comprising the amino acid sequence as denoted by any one of SEQ ID NOs: 5-7.

16. A host cell comprising the chimeric polypeptide according to claim 15.

* * * * *

SEQUENCE LISTING

<160> NUMBER OF SEQ ID NOS: 48

<210> SEQ ID NO 1
<211> LENGTH: 24
<212> TYPE: PRT
<213> ORGANISM: Conus purpurascens
<220> FEATURE:
<221> NAME/KEY: MISC_FEATURE
<222> LOCATION: (3)..(4)
<223> OTHER INFORMATION: X = GAMMA-CARBOXYLGLUTAMYL (GLA)
<220> FEATURE:
<221> NAME/KEY: MISC_FEATURE
<222> LOCATION: (10)..(10)
<223> OTHER INFORMATION: X = GAMMA-CARBOXYLGLUTAMYL (GLA)
<220> FEATURE:
<221> NAME/KEY: MISC_FEATURE
<222> LOCATION: (14)..(14)
<223> OTHER INFORMATION: X = GAMMA-CARBOXYLGLUTAMYL (GLA)
<220> FEATURE:
<221> NAME/KEY: MISC_FEATURE
<222> LOCATION: (23)..(23)
<223> OTHER INFORMATION: X = GAMMA-CARBOXYLGLUTAMYL (GLA)

<400> SEQUENCE: 1

Gly Glu Xaa Xaa His Ser Lys Tyr Gln Xaa Cys Leu Arg Xaa Ile Arg
1               5                   10                  15

Val Asn Lys Val Gln Gln Xaa Cys
            20

<210> SEQ ID NO 2
<211> LENGTH: 17
<212> TYPE: PRT
<213> ORGANISM: Conus geographus
<220> FEATURE:
<221> NAME/KEY: MISC_FEATURE
<222> LOCATION: (3)..(4)
<223> OTHER INFORMATION: X = GAMMA-CARBOXYLGLUTAMYL (GLA)
<220> FEATURE:
<221> NAME/KEY: MISC_FEATURE
<222> LOCATION: (7)..(7)
<223> OTHER INFORMATION: X = GAMMA-CARBOXYLGLUTAMYL (GLA)
<220> FEATURE:
<221> NAME/KEY: MISC_FEATURE
<222> LOCATION: (10)..(10)
<223> OTHER INFORMATION: X = GAMMA-CARBOXYLGLUTAMYL (GLA)
<220> FEATURE:
<221> NAME/KEY: MISC_FEATURE
<222> LOCATION: (14)..(14)

<400> SEQUENCE: 2

Gly Glu Xaa Xaa Leu Gln Xaa Asn Gln Xaa Leu Ile Arg Xaa Lys Ser
1               5                   10                  15

Asn

<210> SEQ ID NO 3
<211> LENGTH: 19
<212> TYPE: PRT
<213> ORGANISM: Conus Parius
<220> FEATURE:
<221> NAME/KEY: misc_feature
<222> LOCATION: (4)..(4)
<223> OTHER INFORMATION: X = GAMMA-CARBOXYLGLUTAMYL (GLA)
<220> FEATURE:
<221> NAME/KEY: misc_feature
<222> LOCATION: (10)..(10)
<223> OTHER INFORMATION: X = GAMMA-CARBOXYLGLUTAMYL (GLA)
<220> FEATURE:
<221> NAME/KEY: misc_feature
<222> LOCATION: (14)..(14)
<223> OTHER INFORMATION: X = GAMMA-CARBOXYLGLUTAMYL (GLA)

<400> SEQUENCE: 3

```
Gly Glu Pro Xaa Val Ala Lys Trp Ala Xaa Gly Leu Arg Xaa Lys Ala
1               5                   10                  15

Ala Ser Asn

<210> SEQ ID NO 4
<211> LENGTH: 24
<212> TYPE: PRT
<213> ORGANISM: Artificial Sequence
<220> FEATURE:
<223> OTHER INFORMATION: Synthetic

<400> SEQUENCE: 4

Gly Glu Glu Glu His Ser Lys Tyr Gln Glu Cys Leu Arg Glu Ile Arg
1               5                   10                  15

Val Asn Lys Val Gln Gln Glu Cys
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic

<400> SEQUENCE: 5

Gly Ala Ala Ala His Ser Lys Tyr Gln Ala Cys Leu Arg Ala Ile Arg
1               5                   10                  15

Val Asn Lys Val Gln Gln Ala Cys
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic

<400> SEQUENCE: 6

Gly Asp Asp Asp His Ser Lys Tyr Gln Asp Cys Leu Arg Asp Ile Arg
1               5                   10                  15

Val Asn Lys Val Gln Gln Asp Cys
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic

<400> SEQUENCE: 7

Gly Gly Gly Gly His Ser Lys Tyr Gln Gly Cys Leu Arg Gly Ile Arg
1               5                   10                  15

Val Asn Lys Val Gln Gln Gly Cys
            20

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8
```

```
Gly Glu Glu Glu Leu Gln Glu Asn Gln Glu Leu Ile Arg Glu Lys Ser
1               5                   10                  15

Asn

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Gly Glu Glu Glu Leu Gln Ala Asn Gln Glu Leu Ile Arg Glu Lys Ser
1               5                   10                  15

Asn

<210> SEQ ID NO 10
<211> LENGTH: 13
<212> TYPE: PRT
<213> ORGANISM: Artificial Sequence
<220> FEATURE:
<223> OTHER INFORMATION: Synthetic

<400> SEQUENCE: 10

Gly Glu Glu Glu Leu Gln Glu Asn Gln Glu Leu Ile Arg
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Gly Glu Glu Glu Leu Gln Ala Asn Gln Glu Leu Ile Arg
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic

<400> SEQUENCE: 12

Gly Ala Ala Ala Leu Gln Ala Asn Gln Ala Leu Ile Arg Ala Lys Ser
1               5                   10                  15

Asn

<210> SEQ ID NO 13
<211> LENGTH: 19
<212> TYPE: PRT
<213> ORGANISM: Artificial Sequence
<220> FEATURE:
<223> OTHER INFORMATION: Synthetic

<400> SEQUENCE: 13

Gly Glu Pro Glu Val Ala Lys Trp Ala Glu Gly Leu Arg Glu Lys Ala
1               5                   10                  15

Ala Ser Asn

<210> SEQ ID NO 14
```

-continued

```
<211> LENGTH: 15
<212> TYPE: PRT
<213> ORGANISM: Artificial Sequence
<220> FEATURE:
<223> OTHER INFORMATION: Synthetic

<400> SEQUENCE: 14

Ala Asp Thr Asp Tyr Ala Asp Gly Ser Glu Asp Lys Val Val Glu
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Synthetic

<400> SEQUENCE: 15

Asn Glu Leu Gln Gln Glu Ser Ile Leu Glu Arg Lys Glu Asn Glu Gly
1               5                   10                  15

Glu

<210> SEQ ID NO 16
<211> LENGTH: 51
<212> TYPE: DNA
<213> ORGANISM: Artificial Sequence
<220> FEATURE:
<223> OTHER INFORMATION: Synthetic

<400> SEQUENCE: 16
aacgagctgc agcaggagag catcctggag aggaaggaga acgagggcga g            51

<210> SEQ ID NO 17
<211> LENGTH: 72
<212> TYPE: DNA
<213> ORGANISM: Artificial Sequence
<220> FEATURE:
<223> OTHER INFORMATION: Synthetic

<400> SEQUENCE: 17
ggcgaagaag agcacagcaa ataccaggag tgcctgaggg agatcagagt caacaaggtg    60
cagcaagaat gt                                                        72

<210> SEQ ID NO 18
<211> LENGTH: 72
<212> TYPE: DNA
<213> ORGANISM: Artificial Sequence
<220> FEATURE:
<223> OTHER INFORMATION: Synthetic

<400> SEQUENCE: 18
ggcgccgccg cccacagcaa gtaccaggcc tgcctgaggg ccatcagggt gaacaaggtg    60
cagcaggcct gc                                                        72

<210> SEQ ID NO 19
<211> LENGTH: 72
<212> TYPE: DNA
<213> ORGANISM: Artificial Sequence
<220> FEATURE:
<223> OTHER INFORMATION: Synthetic

<400> SEQUENCE: 19
ggcgacgacg accacagcaa gtaccaggac tgcctgaggg acatcagggt gaacaaggtg    60
cagcaggact gc                                                        72
```

<210> SEQ ID NO 20
<211> LENGTH: 72
<212> TYPE: DNA
<213> ORGANISM: Artificial Sequence
<220> FEATURE:
<223> OTHER INFORMATION: Synthetic

<400> SEQUENCE: 20
ggcggcggcg gccacagcaa gtaccagggc tgcctgaggg gcatcagggt gaacaaggtg          60
cagcagggct gc                                                              72

<210> SEQ ID NO 21
<211> LENGTH: 51
<212> TYPE: DNA
<213> ORGANISM: Artificial Sequence
<220> FEATURE:
<223> OTHER INFORMATION: Synthetic

<400> SEQUENCE: 21
ggcgaggagg agctgcagga gaaccaggag ctgatcaggg agaagagcaa c                   51

<210> SEQ ID NO 22
<211> LENGTH: 51
<212> TYPE: DNA
<213> ORGANISM: Artificial Sequence
<220> FEATURE:
<223> OTHER INFORMATION: Synthetic

<400> SEQUENCE: 22
ggcgaggagg agctgcaggc caaccaggag ctgatcaggg agaagagcaa c                   51

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
ggcgaggagg agctgcagga gaaccaggag ctgatcagg                                 39

<210> SEQ ID NO 24
<211> LENGTH: 39
<212> TYPE: DNA
<213> ORGANISM: Artificial Sequence
<220> FEATURE:
<223> OTHER INFORMATION: Synthetic

<400> SEQUENCE: 24
ggcgaggagg agctgcaggc caaccaggag ctgatcagg                                 39

<210> SEQ ID NO 25
<211> LENGTH: 51
<212> TYPE: DNA
<213> ORGANISM: Artificial Sequence
<220> FEATURE:
<223> OTHER INFORMATION: Synthetic

<400> SEQUENCE: 25
ggcgccgccg ccctgcaggc caaccaggcc ctgatcaggg ccaagagcaa c                   51

<210> SEQ ID NO 26
<211> LENGTH: 57
<212> TYPE: DNA

-continued

<213> ORGANISM: Artificial Sequence
<220> FEATURE:
<223> OTHER INFORMATION: Synthetic

<400> SEQUENCE: 26
ggcgagcccg aggtggccaa gtgggccgag ggcctgaggg agaaggccgc cagcaac       57

<210> SEQ ID NO 27
<211> LENGTH: 45
<212> TYPE: DNA
<213> ORGANISM: Artificial Sequence
<220> FEATURE:
<223> OTHER INFORMATION: Synthetic

<400> SEQUENCE: 27
gccgacaccg actacgccga cggcagcgag gacaaggtgg tggag                     45

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Asp Glu Lys Asp Ser Glu Ala Val Tyr Val Asp Gly Asp Thr
1               5                   10

<210> SEQ ID NO 29
<211> LENGTH: 21
<212> TYPE: PRT
<213> ORGANISM: Artificial Sequence
<220> FEATURE:
<223> OTHER INFORMATION: Synthetic

<400> SEQUENCE: 29

Met Glu Thr Asp Thr Leu Leu Leu Trp Val Leu Leu Leu Trp Val Pro
1               5                   10                  15

Gly Ser Thr Gly Asp
            20

<210> SEQ ID NO 30
<211> LENGTH: 63
<212> TYPE: DNA
<213> ORGANISM: Artificial Sequence
<220> FEATURE:
<223> OTHER INFORMATION: Synthetic

<400> SEQUENCE: 30
atggagacag acacactcct gctatgggta ctgctgctct gggttccagg ttccactggt     60
gac                                                                   63

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Glu Gln Lys Leu Ile Ser Glu Glu Asp Leu
1               5                   10

<210> SEQ ID NO 32
<211> LENGTH: 30

```
<212> TYPE: DNA
<213> ORGANISM: Artificial Sequence
<220> FEATURE:
<223> OTHER INFORMATION: Synthetic

<400> SEQUENCE: 32
gaacaaaaac tcatctcaga agaggatctg                                                     30

<210> SEQ ID NO 33
<211> LENGTH: 58
<212> TYPE: PRT
<213> ORGANISM: Artificial Sequence
<220> FEATURE:
<223> OTHER INFORMATION: Synthetic

<400> SEQUENCE: 33

Ala Ala Ala Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Gly Gly Gly Ser Gly Gly Gly Gly Ser
    50                  55

<210> SEQ ID NO 34
<211> LENGTH: 174
<212> TYPE: DNA
<213> ORGANISM: Artificial Sequence
<220> FEATURE:
<223> OTHER INFORMATION: Syntehtic

<400> SEQUENCE: 34
gctgcagcag ggggtggggg gtcaggtgga gggggatctg gcggtggagg cagcgggggc          60
ggaggctcag gcggtggcgg aagcggtggg ggaggctctg ggggaggcgg tagcggcggt          120
ggcggcagcg gtggggggcgg ctctgggggt ggtggtagtg gcggcggagg tagt              174

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35

Gly Gly Gly Gly Ser Gly Gly Gly Gly Ser Gly Gly Gly Gly Ser Gly
1               5                   10                  15

Gly Gly Gly Ser
            20

<210> SEQ ID NO 36
<211> LENGTH: 60
<212> TYPE: DNA
<213> ORGANISM: Artificial Sequence
<220> FEATURE:
<223> OTHER INFORMATION: Synthetic

<400> SEQUENCE: 36
ggtggtggcg gaagtggggg cggtggaagt ggtggaggtg ggtccggtgg aggtgggtcc          60

<210> SEQ ID NO 37
<211> LENGTH: 49
<212> TYPE: PRT
```

<213> ORGANISM: Artificial Sequence
<220> FEATURE:
<223> OTHER INFORMATION: Synthetic

<400> SEQUENCE: 37

Ala Val Gly Gln Asp Thr Gln Glu Val Ile Val Val Pro His Ser Leu
1               5                   10                  15

Pro Phe Lys Val Val Val Ile Ser Ala Ile Leu Ala Leu Val Val Leu
            20                  25                  30

Thr Ile Ile Ser Leu Ile Ile Leu Ile Met Leu Trp Gln Lys Lys Pro
        35                  40                  45

Arg

<210> SEQ ID NO 38
<211> LENGTH: 147
<212> TYPE: DNA
<213> ORGANISM: Artificial Sequence
<220> FEATURE:
<223> OTHER INFORMATION: Synthetic

<400> SEQUENCE: 38
gctgtgggcc aggacacgca ggaggtcatc gtggtgccac actccttgcc ctttaaggtg     60
gtggtgatct cagccatcct ggccctggtg gtgctcacca tcatctccct tatcatcctc    120
atcatgcttt ggcagaagaa gccacgg                                        147

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
ttctgctacg agaacgaggt g                                               21

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
agaggcagat cctggaccta c                                               21

<210> SEQ ID NO 41
<211> LENGTH: 17
<212> TYPE: PRT
<213> ORGANISM: Artificial Sequence
<220> FEATURE:
<223> OTHER INFORMATION: Synthetic

<400> SEQUENCE: 41

Gly Glu Asp Asp Leu Gln Asp Asn Gln Asp Leu Ile Arg Asp Lys Ser
1               5                   10                  15

Asn

<210> SEQ ID NO 42
<211> LENGTH: 17
<212> TYPE: PRT
<213> ORGANISM: Artificial Sequence
<220> FEATURE:
<223> OTHER INFORMATION: Synthetic

```
<400> SEQUENCE: 42

Gly Glu Asp Asp Tyr Gln Asp Ala Gln Asp Leu Ile Arg Asp Lys Ser
1               5                   10                  15

Asn

<210> SEQ ID NO 43
<211> LENGTH: 24
<212> TYPE: PRT
<213> ORGANISM: Artificial Sequence
<220> FEATURE:
<223> OTHER INFORMATION: Synthetic

<400> SEQUENCE: 43

Asp Asp Ser Asp Val Trp Trp Gly Gly Ala Asp Thr Asp Tyr Ala Asp
1               5                   10                  15

Gly Ser Glu Asp Lys Val Val Glu
            20

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Ala Asp Thr Asp Tyr Ala Asp Gly Ser Glu Asp
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic

<400> SEQUENCE: 45

Phe Cys Tyr Glu Asn Glu Val
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Arg Gly Arg Ser Trp Thr Tyr
1               5

<210> SEQ ID NO 47
<211> LENGTH: 31
<212> TYPE: PRT
<213> ORGANISM: Artificial Sequence
<220> FEATURE:
<223> OTHER INFORMATION: Synthetic

<400> SEQUENCE: 47

Lys Ser Arg Ile Thr Ser Glu Gly Glu Tyr Ile Pro Leu Asp Gln Ile
1               5                   10                  15

Asp Ile Asn Val Gly Gly Ser Gly Phe Cys Tyr Glu Asn Glu Val
                20                  25                  30
```

-continued

```
<210> SEQ ID NO 48
<211> LENGTH: 93
<212> TYPE: DNA
<213> ORGANISM: Artificial Sequence
<220> FEATURE:
<223> OTHER INFORMATION: Synthetic

<400> SEQUENCE: 48
aagagcagga tcaccagcga gggcgagtac atccccctgg accagatcga catcaacgtg        60
ggcggcagcg gcttctgcta cgagaacgag gtg                                     93
```